United States Patent
Guillemont et al.

(10) Patent No.: US 7,338,949 B2
(45) Date of Patent: Mar. 4, 2008

(54) MYCOBACTERIAL INHIBITORS

(75) Inventors: Jérôme Emile Georges Guillemont, Ande (FR); Elisabeth Therese Jeanne Pasquier, Le Neubourg (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/596,386

(22) PCT Filed: Jan. 21, 2005

(86) PCT No.: PCT/EP2005/050267

§ 371 (c)(1),
(2), (4) Date: Jun. 12, 2006

(87) PCT Pub. No.: WO2005/070924

PCT Pub. Date: Aug. 4, 2005

(65) Prior Publication Data

US 2007/0082895 A1 Apr. 12, 2007

Related U.S. Application Data

(60) Provisional application No. 60/538,768, filed on Jan. 23, 2004.

(51) Int. Cl.
C07D 413/06 (2006.01)
C07D 413/14 (2006.01)
A61K 31/5355 (2006.01)
A61P 31/10 (2006.01)

(52) U.S. Cl. .............. 514/228.8; 514/233.5; 514/233.8; 544/96

(58) Field of Classification Search ............ 544/96; 514/233.5, 233.8, 228.8
See application file for complete search history.

(56) References Cited

U.S. PATENT DOCUMENTS 5,965,572 A 10/1999 Ellis et al.

FOREIGN PATENT DOCUMENTS

WO   WO 00/34265 A2   6/2000
WO   WO 04/011436 A1  2/2004

OTHER PUBLICATIONS

Hackh's Chemical Dictionary, 4th Edition, edited by J. Grant (1972), McGraw Hill, New York (p. 27).*

* cited by examiner

*Primary Examiner*—Kahsay Habte
(74) *Attorney, Agent, or Firm*—Thomas Dodd

(57) ABSTRACT

The present invention relates to novel substituted quinoline derivatives according to the general formula (Ia) or the general formula (Ib)

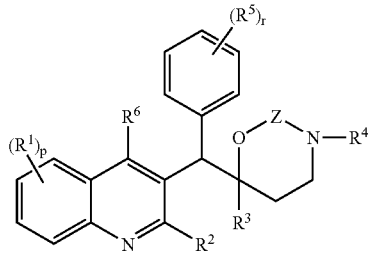

(Ia)

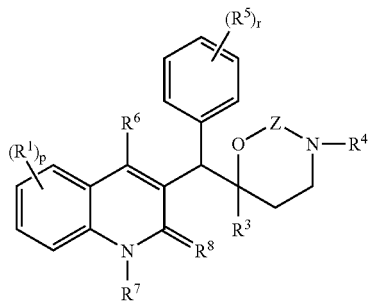

(Ib)

salts, quaternary amines, stereochemically isomeric forms, tautomeric forms and N-oxide forms thereof, wherein $R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl; p is 1, 2, 3 or 4; $R^2$ is hydrogen, hydroxy, thio, alkyloxy, alkyloxyalkyloxy, alkylthio, mono or di(alkyl)amino or a radical of formula

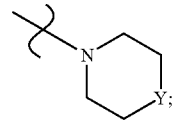

$R^3$ is alkyl, Ar, Ar-alkyl, Het or Het-alkyl; $R^4$ is hydrogen, alkyl or benzyl; $R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^5$ radicals may be taken together to form together with the phenyl ring to which they are attached a naphthyl; r is 1, 2, 3, 4 or 5; $R^6$ is hydrogen, alkyl, Ar or Het; $R^7$ is hydrogen or alkyl; $R^8$ is oxo; or $R^7$ and $R^8$ taken together form the radical —CH═CH—N═; Z is $CH_2$ or C(═O). The claimed compounds are useful for the treatment of mycobacterial diseases, particularly those diseases caused by pathogenic mycobacteria such as *M. tuberculosis, M. bovis, M. avium, M. smegmatis* and *M. marinum*. Also claimed is a pharmaceutical composition containing a compound of the present invention, the use of the claimed compounds or compositions for the manufacture of a medicament for the treatment of mycobacterial diseases and a process for preparing the claimed compounds.

9 Claims, No Drawings

MYCOBACTERIAL INHIBITORS

This application is a 371 of PCT/EP05/50267 filed Jan. 21, 2005 which claims benefit of U.S. provisional application Ser. No. 60/538,768 filed Jan. 23, 2004.

The present invention relates to novel substituted quinoline derivatives useful for the treatment of mycobacterial diseases, particularly those diseases caused by pathogenic mycobacteria such as Mycobacteria (M.) tuberculosis, M. bovis, M. avium and M. marinum.

BACKGROUND OF THE INVENTION

Mycobacterium tuberculois is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of M. tuberculosis, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together, the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and can not be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against MDR strains.

The term "drug resistant" as used hereinbefore or hereinafter is a term well understood by the person skilled in microbiology. A drug resistant Mycobacterium is a Mycobacterium which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs.

MDR tuberculosis is a specific form of drug resistant tuberculosis due to a bacterium resistant to at least isoniazid and rifampicin (with or without resistance to other drugs), which are at present the two most powerful anti-TB drugs.

The purpose of the present invention is to provide novel compounds, in particular substituted quinoline derivatives, having the property of inhibiting growth of Mycobacteria including drug resistant or multi drug resistant Mycobacteria, and therefore useful for the treatment of mycobacterial diseases, particularly those diseases caused by pathogenic mycobacteria such as Mycobacterium tuberculosis, M. bovis, M. avium, M. smegmatis and M. marinum.

Substituted quinolines were already disclosed in U.S. Pat. No. 5,965,572 (The United States of America) for treating antibiotic resistant infections and in WO 00/34265 to inhibit the growth of bacterial microorganisms. None of these publications disclose the substituted quinoline derivatives according to our invention.

SUMMARY OF THE INVENTION

The present invention relates to novel substituted quinoline derivatives according to Formula (Ia) and (Ib)

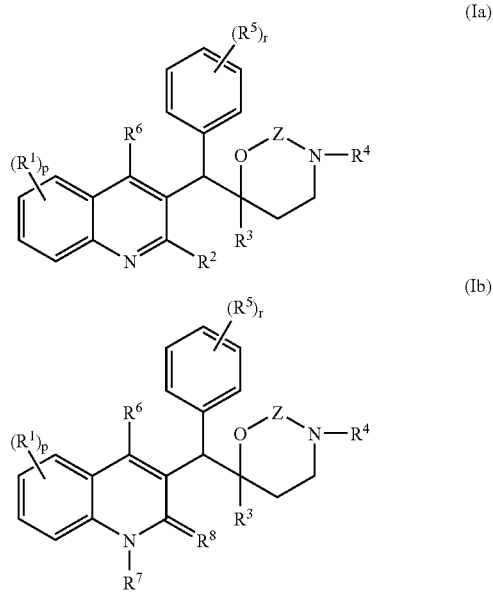

the pharmaceutically acceptable acid or base addition salts thereof, the quaternary amines thereof, the stereochemically isomeric forms thereof, the tautomeric forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4;

$R^2$ is hydrogen, hydroxy, thio, alkyloxy, alkyloxyalkyloxy, alkylthio, mono or di(alkyl)amino or a radical of formula

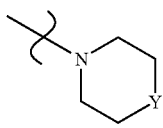

wherein Y is $CH_2$, O, S, NH or N-alkyl;

$R^3$ is alkyl Ar, Ar-alkyl, Het or Het-alkyl;

$R^4$ is hydrogen, alkyl or benzyl;

$R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl; or two vicinal $R^5$ radicals may be taken together to form together with the phenyl ring to which they are attached a naphthyl;

r is an integer equal to 1, 2, 3, 4 or 5; and $R^6$ is hydrogen, alkyl, Ar or Het;

$R^7$ is hydrogen or alkyl;

$R^8$ is oxo; or $R^7$ and $R^8$ together form the radical —CH=CH—N=;

Z is $CH_2$ or C(=O);

alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl haloalkyl, alkyloxy, haloalkyloxy, carboxyl, alkyloxycarbonyl, aminocarbonyl morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl indolyl, benzimidazolyl, benzoxazolyl, benzisoxazolyl, benzothiazolyl, benzisothiazolyl, benzofuranyl, benzothienyl 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;

halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms.

The compounds according to Formula (Ia) and (Ib) are interrelated in that e.g. a compound according to Formula (Ib), with $R^8$ equal to oxo is the tautomeric equivalent of a compound according to Formula (Ia) with $R^2$ equal to hydroxy (keto-enol tautomerism).

DETAILED DESCRIPTION

In the framework of this application, alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo. Preferably, alkyl is methyl, ethyl or cyclohexylmethyl.

In the framework of this application, Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl haloalkyl alkyloxy, haloalkyloxy, carboxyl, alkyloxycarbonyl, aminocarbonyl morpholinyl and mono- or dialkylaminocarbonyl. Preferably, Ar is naphthyl or phenyl, each optionally substituted with 1 or 2 halo substituents.

In the framework of this application, Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy. Preferably, Het is thienyl or furanyl or pyridyl, most preferably Het is furanyl.

In the framework of this application, halo is a substituent selected from the group of fluoro, chloro, bromo and iodo and haloalkyl is a straight or branched saturated hydrocarbon radical having from 1 to 6 carbon atoms or a cyclic saturated hydrocarbon radical having from 3 to 6 carbon atoms, wherein one or more carbon atoms are substituted with one or more halo-atoms. Preferably, halo is bromo, fluoro or chloro and preferably, haloalkyl is trifluoromethyl.

Whenever used hereinafter, the term "compounds of formula (Ia) or (Ib)" is meant to also include their N-oxide forms, their salts, their quaternary amines, their tautomeric forms and their stereochemically isomeric forms. Of special interest are those compounds of formula (Ia) or (Ib) which are stereochemically pure.

An interesting embodiment of the present invention relates to those compounds of formula (Ia) or (Ib), the pharmaceutically acceptable acid or base addition salts thereof, the stereochemically isomeric forms thereof, the tautomeric forms thereof and the N-oxide forms thereof, wherein Z is $CH_2$;

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1, 2, 3 or 4;

R² is hydrogen, hydroxy, thio, alkyloxy, alkyloxyalkyloxy, alkylthio, mono or di(alkyl)amino or a radical of formula

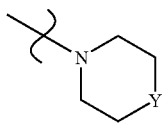

wherein Y is CH₂, O, S, NH or N-alkyl;
R³ is alkyl, Ar, Ar-alkyl, Het or Het-alkyl;
R⁴ is hydrogen, alkyl or benzyl;
R⁵ is hydrogen, halo, haloalkyl, hydroxy, Ar, alkyl, alkyloxy, alkylthio, alkyloxyalkyl, alkylthioalkyl, Ar-alkyl or di(Ar)alkyl; or
two vicinal R⁵ radicals may be taken together to form together with the phenyl ring to which they are attached a naphthyl;
r is an integer equal to 1, 2, 3, 4 or 5; and
R⁶ is hydrogen, alkyl, Ar or Het;
R⁷ is hydrogen or alkyl;
R⁸ is oxo; or
R⁷ and R⁸ together form the radical —CH=CH—N=;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo, hydroxy, alkyloxy or oxo;
Ar is a homocycle selected from the group of phenyl naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl morpholinyl and mono- or dialkylaminocarbonyl;
Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy;
halo is a substituent selected from the group of fluoro, chloro, bromo and iodo and
haloalkyl is a straight or branched saturated hydrocarbon radical having from 1 to 6 carbon atoms or a cyclic saturated hydrocarbon radical having from 3 to 6 carbon atoms, wherein one or more carbonatoms are substituted with one or more halo-atoms.
Preferably, R⁵ is hydrogen, halo, haloalkyl, hydroxy, Ar, alkyl, alkyloxy, alkylthio, alkyloxyalkyl, alkylthioalkyl, Ar-alkyl or di(Ar)alkyl.

Preferably, the invention relates to compounds of Formula (Ia) or (Ib) wherein:
R¹ is hydrogen, halo, cyano, Ar, Het, alkyl, and alkyloxy;
p is an integer equal to 1, 2, 3 or 4;
R² is hydrogen, hydroxy, alkyloxy, alkyloxyalkyloxy, alkylthio or a radical of formula

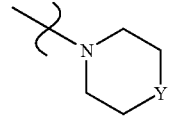

wherein Y is O;
R³ is alkyl, Ar, Ar-alkyl or Het;
R⁴ is hydrogen, alkyl or benzyl;
R⁵ is hydrogen, halo or alkyl; or
two vicinal R⁵ radicals may be taken together to form together with the phenyl ring to which they are attached a naphthyl;
r is an integer equal to 1; and
R⁶ is hydrogen;
R⁷ is hydrogen or alkyl;
R⁸ is oxo; or
R⁷ and R⁸ together form the radical —CH=CH—N=;
alkyl is a straight or branched saturated hydrocarbon radical having from 1 to 6 carbon atoms; or is a cyclic saturated hydrocarbon radical having from 3 to 6 carbon atoms; or is a a cyclic saturated hydrocarbon radical having from 3 to 6 carbon atoms attached to a straight or branched saturated hydrocarbon radical having from 1 to 6 carbon atoms; wherein each carbon atom can be optionally substituted with halo or hydroxy;
Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl;
Het is a monocyclic heterocycle selected from the group of N-phenoxypiperidinyl, furanyl, thienyl, pyridinyl, pyrimidinyl; or a bicyclic heterocycle selected from the group of benzothienyl, 2,3-dihydrobenzo[1,4]dioxinyl or benzo[1,3]-dioxolyl; each monocyclic and bicyclic heterocycle may optionally be substituted on a carbon atom with 1, 2 or 3 alkyl substituents; and
halo is a substituent selected from the group of fluoro, chloro and bromo.
For compounds according to either Formula (Ia) or (Ib), preferably, R¹ is hydrogen, halo, Ar, Het, alkyl or alkyloxy. More preferably, R¹ is halo. Most preferably, R¹ is bromo.
Preferably, p is equal to 1.
Preferably, R² is hydrogen, alkyloxy or alkylthio. More preferably, R² is alkyloxy. Most preferably, R² is methyloxy.
Preferably, R³ is naphthyl, phenyl or Het, each optionally substituted with 1 or 2 substituents, that substituent preferably being a halo or haloalkyl, most preferably being a halo. More preferably, R³ is naphthyl or phenyl. Most preferably, R³ is naphthyl.
Preferably, R⁴ is hydrogen or alkyl more preferably alkyl, such as methyl or ethyl. Most preferably R⁴ is methyl.
Preferably, R⁵ is hydrogen, alkyl or halo. Most preferably, R⁵ is hydrogen
Preferably r is 1 or 2.

Preferably, $R^6$ is hydrogen or methyl. Most preferably, $R^6$ is hydrogen.

Preferably, Z is $CH_2$.

Preferably, Z is C(=O).

For compounds according to Formula (Ib) only, preferably, $R^7$ is alkyl, preferably methyl, and $R^8$ is oxygen.

An interesting group of compounds are the compounds of Formula (Ia), the pharmaceutically acceptable acid or base addition salts thereof, the quaternary amines thereof, the stereochemically isomeric forms thereof, the tautomeric forms thereof and the N-oxide forms thereof.

An interesting group of compounds are those compounds according to Formula (Ia), the pharmaceutically acceptable acid or base addition salts thereof, the quaternary amines thereof, the stereochemically isomeric forms thereof the tautomeric forms thereof and the N-oxide forms thereof, in which $R^1$ is hydrogen, halo, Ar, Het, alkyl or alkyloxy; p=1; $R^2$ is hydrogen, alkyloxy or alkylthio; $R^3$ is naphthyl, phenyl or Het, each optionally substituted with 1 or 2 substituents selected from the group of halo and haloalkyl; $R^4$ is hydrogen or alkyl; $R^5$ is hydrogen, alkyl or halo; r is equal to 1 and $R^6$ is hydrogen.

An interesting group of compounds are those compounds according to Formula (Ia) wherein $R^1$ is hydrogen; halo, e.g. bromo; alkyl, e.g. methyl; or Het, e.g. furanyl; $R^2$ is alkyloxy, e.g. methyloxy; $R^3$ is naphthyl, phenyl or Het, each optionally substituted with halo, e.g. phenyl optionally substituted with halo, naphthyl or furanyl; $R^4$ is alkyl e.g. methyl or ethyl; $R^5$ is hydrogen or halo, e.g. chloro; $R^6$ is hydrogen; Z is $CH_2$ or C(=O).

The pharmaceutically acceptable acid addition salts are defined to comprise the therapeutically active non-toxic acid addition salt forms which the compounds according to either Formula (Ia) or (Ib) are able to form. Said acid addition salts can be obtained by treating the base form of the compounds according to either Formula (Ia) or (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds according to either Formula (Ia) or (Ib) containing acidic protons may also be converted into their therapeutically active non-toxic base addition salt forms by treatment with appropriate organic and inorganic bases. Appropriate base salts forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said acid or base addition salt forms can be converted into the free forms by treatment with an appropriate base or acid.

The term addition salt as used in the framework of this application also comprises the solvates which the compounds according to either Formula (Ia) or (Ib) as well as the salts thereof, are able to form. Such solvates are, for example, hydrates and alcoholates.

The term "quaternary amine" as used hereinbefore defines the quaternary ammonium salts which the compounds of formula (Ia) or (Ib) are able to form by reaction between a basic nitrogen of a compound of formula (Ia) or (Ib) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "stereochemically isomeric forms" as used herein defines all possible isomeric forms which the compounds of either Formula (Ia) or (Ib) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Stereochemically isomeric forms of the compounds of either Formula (Ia) or (Ib) are obviously intended to be embraced within the scope of this invention.

Following CAS-nomenclature conventions, when two stereogenic centers of known absolute configuration are present in a molecule, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the molecule has an S configuration and the second center is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

Compounds of either Formula (Ia) or (Ib) and some of the intermediate compounds invariably have at least two stereogenic centers in their structure which may lead to at least 4 stereochemically different structures.

The compounds of either Formula (Ia) or (Ib) as prepared in the processes described below may be synthesized in the form of racemic mixtures of enantiomers which can be separated from one another following art-known resolution procedures. The racemic compounds of either Formula (Ia) or (Ib) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of either Formula (Ia) or (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of either Formula (Ia) or (Ib) are meant to comprise those compounds of either Formula (Ia) or (Ib) wherein e.g. an enol group is converted into a keto group keto-enol tautomerism).

The N-oxide forms of the compounds according to either Formula (Ia) or (Ib) are meant to comprise those compounds of either Formula (Ia) or (Ib) wherein one or several nitrogen atoms are oxidized to the so-called N-oxide, particularly those N-oxides wherein the nitrogen of the amine radical is oxidized.

The invention also comprises derivative compounds (usually called "pro-drugs") of the pharmacologically-active compounds according to the invention, which are degraded in vivo to yield the compounds according to the invention. Pro-drugs are usually (but not always) of lower potency at the target receptor than the compounds to which they are degraded. Prodrugs are particularly useful when the desired compound has chemical or physical properties that make its administration difficult or inefficient. For example, the desired compound may be only poorly soluble, it may be poorly transported across the mucosal epithelium, or it may have an undesirably short plasma half-life. Further discussion on pro-drugs may be found in Stella, V. J. et. al., "Prodrugs", *Drug Delivery Systems,* 1985, pp. 112-176, and *Drugs,* 1985, 29, pp. 455-473.

Pro-drugs forms of the pharmacologically-active compounds according to the invention will generally be compounds according to either Formula (Ia) or (Ib), the pharmaceutically acceptable acid or base addition salts thereof, the stereochemically isomeric forms thereof, the tautomeric forms thereof and the N-oxide forms thereof, having an acid group which is esterified or amidated. Included in such esterified acid groups are groups of the formula —COOR$^x$, where R$^x$ is a C$_{1-6}$alkyl, phenyl, benzyl or one of the following groups:

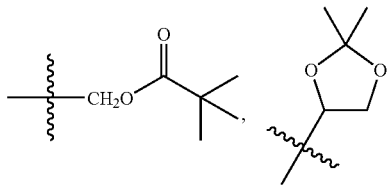

Amidated groups include groups of the formula —CONR$^y$R$^z$, wherein R$^y$ is H, C$_{1-6}$alkyl, phenyl or benzyl and R$^z$ is —OH, H, C$_{1-6}$alkyl, phenyl or benzyl.

Compounds according to the invention having an amino group may be derivatised with a ketone or an aldehyde such as formaldehyde to form a Mannich base. This base will hydrolyze with first order kinetics in aqueous solution.

The compounds according to the invention have surprisingly been shown to be suitable for the treatment of mycobacterial diseases, particularly those diseases caused by pathogenic mycobacteria, including drug resistant and multi drug resistant mycobacteria, such as *Mycobacterium tuberculosis, M. bovis, M. avium, M. smegmatis* and *M. marinum*. The present invention thus also relates to compounds of either Formula (Ia) or (Ib) as defined hereinabove, the pharmaceutically acceptable acid or base addition salts thereof, the stereochemically isomeric forms thereof, the tautomeric forms thereof and the N-oxide forms thereof, for use as a medicine.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight of the active ingredient of formula (Ia) or (Ib), and, from 1 to 99.95% by weight, more preferably from 30 to 99.9 weight % of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Further, the present invention also relates to the use of a compound of either Formula (Ia) or (Ib), the pharmaceutically acceptable acid or base addition salts thereof, the stereochemically isomeric forms thereof, the tautomeric forms thereof and the N-oxide forms thereof, as well as any of the aforementioned pharmaceutical compositions thereof for the manufacture of a medicament for the prevention or the treatment of mycobacterial diseases.

Accordingly, in another aspect, the invention provides a method of treating a patient suffering from, or at risk of, a mycobacterial disease, which comprises administering to the patient a therapeutically effective amount of a compound or pharmaceutical composition according to the invention.

The compounds of the present invention may also be combined with one or more other antimycobacterial agents.

Therefore, the present invention also relates to a combination of (a) a compound of formula (Ia) or (Ib) and (b) one or more other antimycobacterial agents.

The present invention also relates to a combination of (a) a compound of formula (Ia) or (Ib) and (b) one or more other antimycobacterial agents for use as a medicine.

A pharmaceutical composition comprising a pharmaceutically acceptable carrier and, as active ingredient, a therapeutically effective amount of (a) a compound of formula (Ia) or (Ib) and (b) one or more other antimycobacterial agents is also comprised by the present invention.

The other Mycobacterial agents which may be combined with the compounds of formula (Ia) or (Ib) are for example rifampicin (=rifampin); isoniazid; pyrazinamide; amikacin; ethionamide; moxifloxacin; ethambutol; streptomycin; para-aminosalicylic acid; cycloserine; capreomycin; kanamycin; thioacetazone; PA-824; quinolones/fluoroquinolones such as for example ofloxacin, ciprofloxacin, sparfloxacin; macrolides such as for example clarithromycin, clofazimine, amoxycillin with clavulamic acid; rifamycins; rifabutin; rifapentine.

Preferably, the present compounds of formula (Ia) or (Ib) are combined with rifapentin and moxifloxacin.

General Preparation

The compounds according to the invention can generally be prepared by a succession of steps, each of which is known to the skilled person.

Compounds of formula (Ia) and (Ib) wherein Z is $CH_2$, said compounds being represented by formula (Ia-1) and (Ib-1), can be prepared by reacting an intermediate of formula (II-a) and (II-b) with paraformaldehyde in a suitable solvent, such as for example toluene.

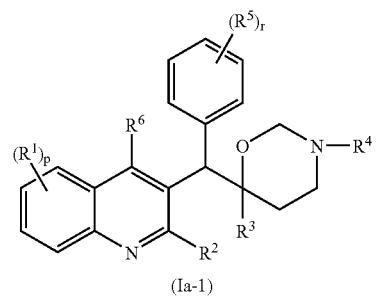

(Ia-1)

(II-b)

(Ib-1)

Compounds of formula (Ia) and (Ib) wherein Z is C(=O), said compounds being represented by formula (Ia-2) and (Ib-2), can be prepared by reacting an intermediate of formula (III-a) and (III-b) wherein $W_1$ represents a suitable leaving group, such as for example imidazole, alkoxy groups, e.g. methoxy, with a suitable base, such as for example sodium hydride, potassium tertiobutylate, in a suitable solvent, such as for example tetrahydrofuran, diethylether, dioxane.

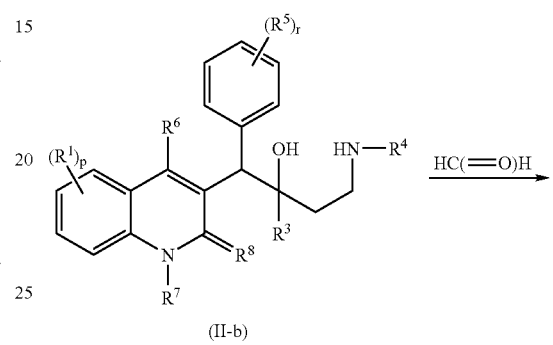

(II-a)

(III-a)

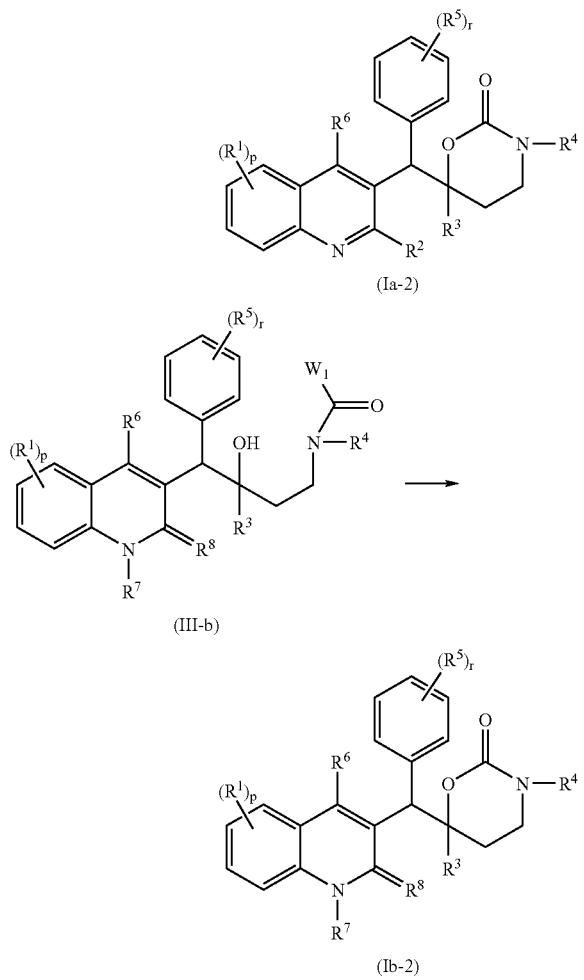

In the above reactions, the obtained compound of formula (Ia) or (Ib) can be isolated, and, if necessary, purified according to methodologies generally known in the art such as, for example, extraction, crystallization, distillation, trituration and chromatography. In case the compound of formula (Ia) or (Ib) crystallizes out, it can be isolated by filtration. Otherwise, crystallization can be caused by the addition of an appropriate solvent, such as for example water; acetonitrile; an alcohol, such as for example methanol, ethanol; and combinations of said solvents. Alternatively, the reaction mixture can also be evaporated to dryness, followed by purification of the residue by chromatography (e.g. reverse phase HPLC, flash chromatography and the like). The reaction mixture can also be purified by chromatography without previously evaporating the solvent. The compound of formula (Ia) or (Ib) can also be isolated by evaporation of the solvent followed by recrystallisation in an appropriate solvent, such as for example water; acetonitrile; an alcohol, such as for example methanol; and combinations of said solvents.

The person skilled in the art will recognise which method should be used, which solvent is the most appropriate to use or it belongs to routine experimentation to find the most suitable isolation method.

The compounds of formula (Ia) or (Ib) may further be prepared by converting compounds of formula (Ia) or (Ib) into each other according to art-known group transformation reactions.

The compounds of formula (Ia) or (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (Ia) or (Ib) wherein $R^4$ is alkyl, may be converted into a suitable quaternary amine by reaction with a suitable quaternizing agent, such as, for example, an optionally substituted alkylhalide, e.g. $ICH_3$, in the presence of a suitable solvent, such as for example acetone.

Some of the compounds of formula (I) and some of the intermediates in the present invention may consist of a mixture of stereochemically isomeric forms. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

It is to be understood that in the above or the following preparations, the reaction products may be isolated from the reaction medium and, if necessary, further purified according to methodologies generally known in the art such as, for example, extraction, crystallization, distillation, trituration and chromatography.

Some of the intermediates and starting materials are known compounds and may be commercially available or may be prepared according to art-known procedures.

Intermediates of formula (II-a) and (II-b) can be prepared by reacting an intermediate of formula (IV-a) and (IV-b) with a suitable deprotecting agent, such as for example 1-chloroethyl chloroformate, in a suitable solvent, such as for example 1,2-dichloroethane and a suitable alcohol, such as for example methanol and the like.

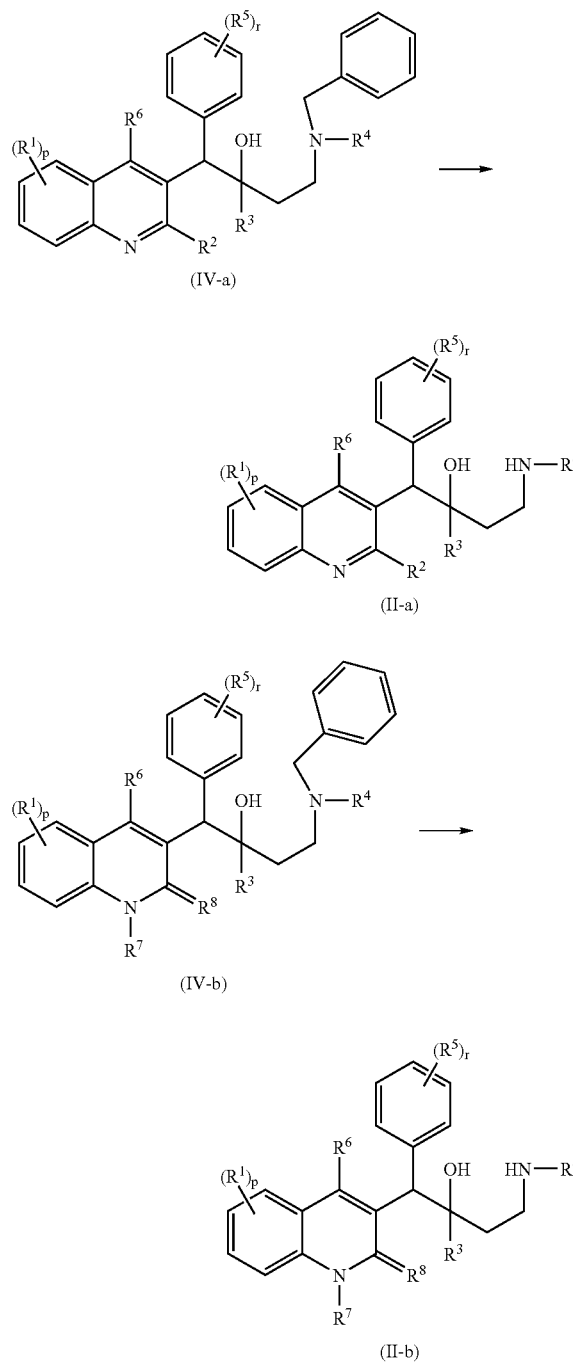

Intermediates of formula (II-a) or (II-b) can also be prepared by reacting an intermediate of formula (IV-a) or (IV-b) with ammonium formate in the presence of palladium on charcoal and in the presence of a suitable solvent, such as for example an alcohol, e.g. methanol. Intermediates of formula (IV-a) or (IV-b) wherein $R^1$ is halo, may loose said halo substituent during their transformation to intermediates of formula (II-a) or (II-b).

Intermediates of formula (IV-a) and (IV-b) can be prepared by reacting an intermediate of formula (V-a) and (V-b) with an intermediate of formula (VI) in the presence of a suitable reducing agent, such as for example n-BuLi in the presence of a suitable base, such as for example N,N-diisopropylamine, and in the presence of a suitable solvent, such as for example tetrahydrofuran.

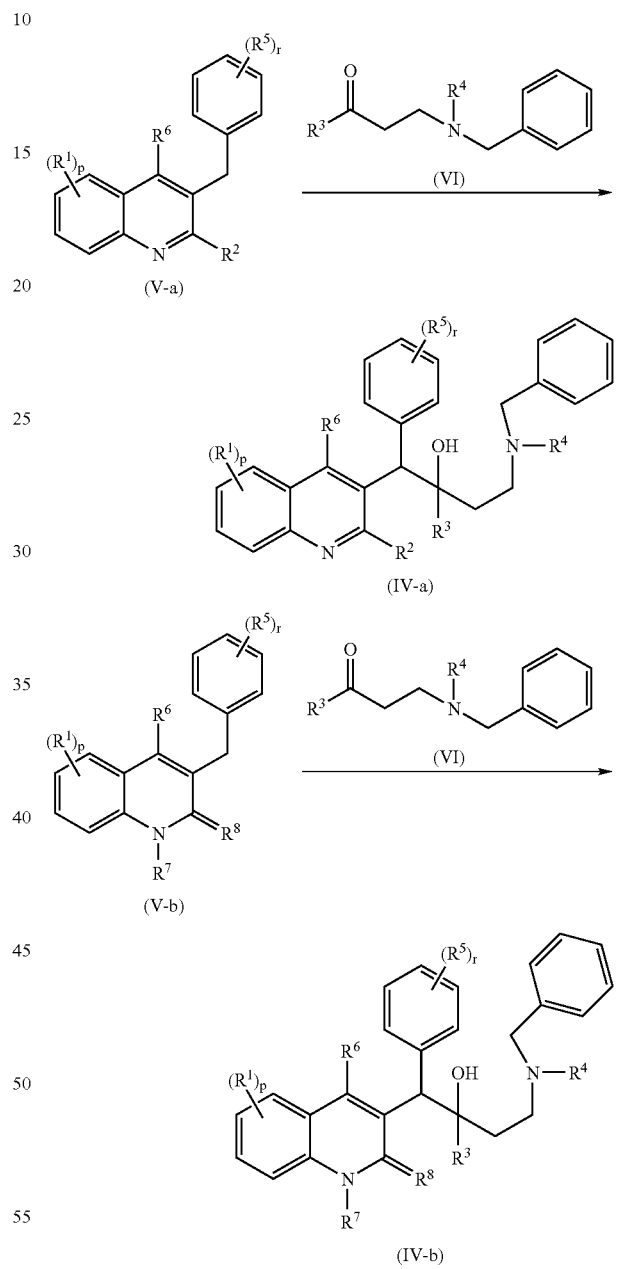

Intermediates of formula (IV-a) or (IV-b) wherein $R^1$ represents Het and p is 1, said intermediates being represented by formula (IV-a-1) or (IV-b-1), can be prepared by reacting an intermediate of formula (IV-a) or (IV-b) wherein $R^1$ represents halo, said intermediates being represented by formula (IV-a-2) or (IV-b-2), with an intermediate of formula (VII) in the presence of a suitable catalyst, such as for example Pd(PPh$_3$)$_4$, a suitable base, such as for example K$_2$CO$_3$, and a suitable solvent, such as for example dimethylether and a suitable alcohol, such as for example methanol and the like.

sents the remaining of the intermediate, such as for example 1,1'-carbonylbis-1H-imidazole, methylchloroformiate or ethylchloroformiate, in the presence of a suitable solvent, such as for example tetrahydrofuran.

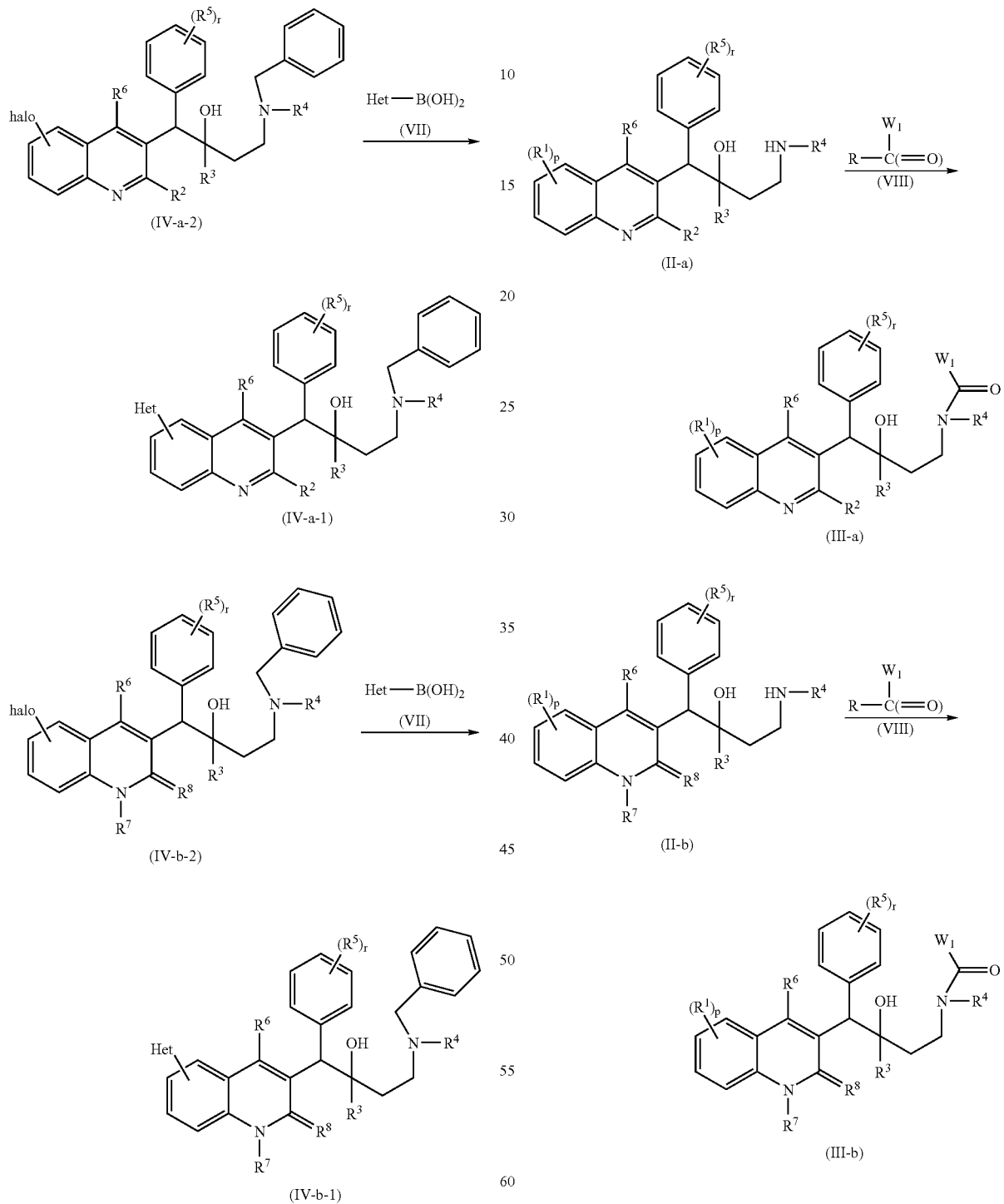

Intermediates of formula (III-a) or (III-b) can be prepared by reacting an intermediate of formula (II-a) or (II-b) with an intermediate of formula (VIII) wherein W$_1$—(C=O) represents the group that has to be introduced and R repre- The intermediate compounds of formula (V-a) or (V-b) are compounds that are either commercially available or may be prepared according to conventional reaction procedures generally known in the art. For example, intermediates of formula (V-a-1) may be prepared according to the following reaction scheme (1):

Scheme 1

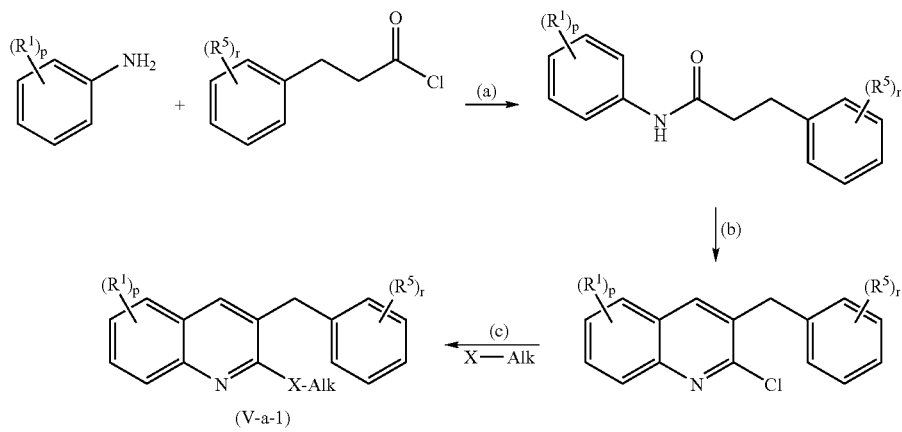

wherein all variables are defined as in Formula (Ia) and (Ib). Reaction scheme (1) comprises step (a) in which an appropriately substituted aniline is reacted with an appropriate acylchloride such as 3-phenylpropionyl chloride, 3-fluorobenzenepropionyl chloride or p-chlorobenzenepropionyl chloride, in the presence of a suitable base, such as triethylamine and a suitable reaction-inert solvent, such as methylene chloride or ethylene dichloride. The reaction may conveniently be carried out at a temperature ranging between room temperature and reflux temperature. In a next step (b) the adduct obtained in step (a) is reacted with phosphoryl chloride POCl$_3$) in the presence of a suitable solvent, such as for example N,N-dimethylformamide (Vilsmeier-Haack formylation followed by cyclization). The reaction may conveniently be carried out at a temperature ranging between room temperature and reflux temperature. In a next step (c) a specific R$^2$-group, wherein R$^2$ is an alkyloxy or alkylthio radical is introduced by reacting the intermediate compound obtained in step (b) with a compound —X—Alk, wherein X=S or O and Alk is an alkylgroup as defined in Formula (Ia) and (Ib), such as for example sodium methanolate, in the presence of a suitable solvent, such as for example an alcohol, e.g. methanol.

Intermediates according to Formula (V-a-2) may be prepared according to the following reaction scheme (2), wherein in a first step (a) a substituted indole-2,3-dione is reacted with a substituted 3-phenylpropionaldehyde in the presence of a suitable base such as sodium hydroxide (Pfitzinger reaction), after which the carboxylic acid compound in a next step (b) is decarboxylated at high temperature in the presence of a suitable reaction-inert solvent such as diphenylether.

Scheme 2

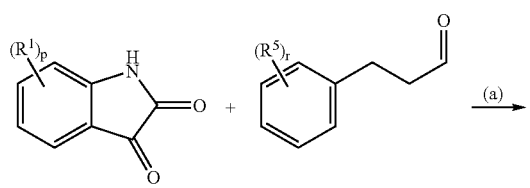

-continued

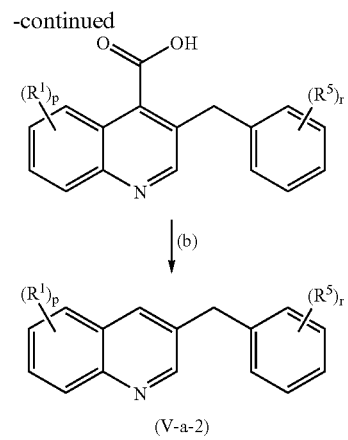

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC. Typically, compounds of Formula (Ia) and (Ib) may be separated into their isomeric forms.

The intermediates of Formula (VI) are compounds that are either commercially available or may be prepared according to conventional reaction procedures generally known in the art. For example, intermediate compounds of Formula (VI) may be prepared according to the following reaction scheme (3):

Scheme 3

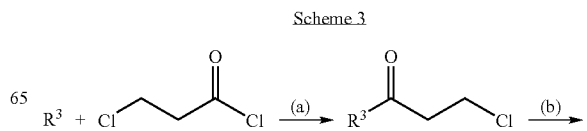

-continued

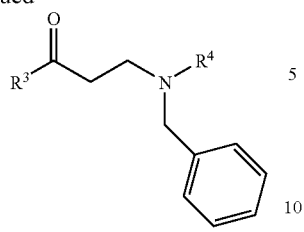

Reaction scheme (3) comprises step (a) in which R³, for example an appropriately substituted phenyl, naphthyl, or Het, is reacted by Friedel-Craft reaction with an appropriate acylchloride such as 3-chloropropionyl chloride or 4-chlorobultyryl chloride, in the presence of a suitable Lewis acid, such as AlCl₃, FeCl₃, SnCl₄, TiCl₄ or ZnCl₂ and optionally a suitable reaction-inert solvent, such as methylene chloride or ethylene dichloride. The reaction may conveniently be carried out at a temperature ranging between room temperature and reflux temperature. In a next step (b) an amino group (—NR₄(CH₂-C₆H₅) is introduced by reacting the intermediate compound obtained in step (a) with a primary or secondary amine, in the presence of a suitable solvent, such as for example acetonitrile, and optionally in the presence of a suitable base, such as for example K₂CO₃.

The following examples illustrate the present invention without being limited thereto.

Experimental Part

Of some compounds the absolute stereochemical configuration of the stereogenic carbon atom(s) therein was not experimentally determined. In those cases the stereochemically isomeric form which was first isolated is designated as "A" and the second as "B", without further reference to the actual stereochemical configuration. However, said "A" and "B" isomeric forms can be unambiguously characterized by a person skilled in the art, using art-known methods such as, for example, X-ray diffraction. The isolation method is described in detail below.

For some of the intermediates and some of the final compounds, stereochemical configurations are indicated in the structures. These configurations are relative configurations indicating that the groups concerned are located in the same or opposite plane of the molecule (↘↘=same plane; ↘↖=opposite plane)

\*R means that the chiral center is absolute R or absolute S.

\*S means that the chiral center is absolute R or absolute S.

Experimental Part

Hereinafter, the term 'M.P." means melting point, 'THF' means tetrahydrofuran, 'EtOAc' means ethyl acetate, 'MeOH' means methanol, 'DME' means dimethyl ether, 'DIPE' means diisopropyl ether, 'DMF' means N,N-dimethylformamide, 'Et₃N' means triethylamine, 'Pd(PPh₃)₄' means tetrakis(triphenylphosphine)palladium, 'CDI' means 1,1'-carbonylbis-1H-imidazole.

A. Preparation of the Intermediates

EXAMPLE A1

Preparation of intermediate 1

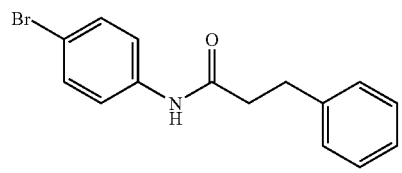

Intermediate 1

Benzenepropanoylchloride (0.488 mol) was added dropwise at room temperature to a solution of 4-bromobenzenamine (0.407 mol) in Et₃N (70 ml) and CH₂Cl₂ (700 ml) and the mixture was stirred at room temperature overnight. The mixture was poured out into water and concentrated NH₄OH, and extracted with CH₂Cl₂. The organic layer was dried (MgSO₄), filtered, and the solvent was evaporated. The residue was crystallized from diethyl ether. The residue (119.67 g) was taken up in CH₂Cl₂ and washed with HCl 1N. The organic layer was dried (MgSO₄), filtered, and the solvent was evaporated. Yield: 107.67 g of intermediate 1.

EXAMPLE A2

Preparation of intermediate 2

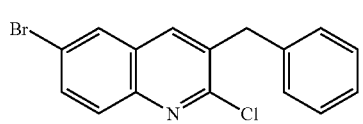

Intermediate 2

The reaction was carried out twice. POCl₃ (1.225 mol) was added dropwise at 10° C. to DMF (0.525 mol). Then intermediate 1 (0.175 mol) was added at room temperature. The mixture was stirred overnight at 80° C., poured out on ice and extracted with CH₂Cl₂. The organic layer was dried (MgSO₄), filtered, and the solvent was evaporated, yielding 77.62 g (67%) of intermediate 2. The product was used without further purification.

EXAMPLE A3

Preparation of intermediate 3

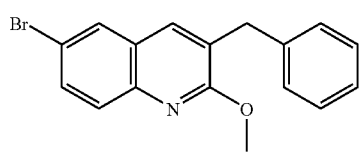

Intermediate 3

A mixture of intermediate 2 (0.233 mol) in CH₃ONa (30%) in MeOH (222.32 ml) and MeOH (776 ml) was stirred and refluxed overnight, then poured out on ice and extracted with CH₂Cl₂. The organic layer was separated, dried (MgSO₄), filtered and the solvent was evaporated. The residue was purified by column chromatography over silica gel (eluent: CH₂Cl₂/cyclohexane 20/80 and then 100/0; 20-45 μm). The pure factions were collected and the solvent was evaporated. Yield: 25 g (33%) of intermediate 3 (M.P.: 84° C.).

EXAMPLE A4 a) Preparation of intermediates 4 and 5

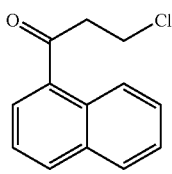

Intermediate 4

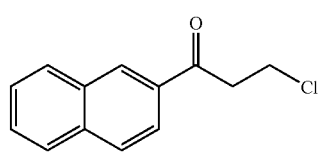

Intermediate 5

A mixture of aluminium chloride (34.3 g, 0.257 mol) and 3-chloropropanoyl chloride (29.7 g, 0.234 mol) in 1,2-dichloroethane (150 ml) was stirred at 0° C. A solution of naphthalene (30 g, 0.234 mol) in 1,2-dichloroethane (50 ml) was added. The mixture was stirred at 5° C. for 2 hours and poured out into ice water. The organic layer was separated, dried (MgSO₄), filtered, and the solvent was evaporated. The residue (56 g) was purified by column chromatography over silica gel (eluent cyclohexane/CH₂Cl₂: 60/40; 20-45 μm). Two fractions were collected and the solvent was evaporated to afford intermediate 4 (31 g, 61%) as an oil. The second fraction (14 g) was taken up in DIPE to afford intermediate 5 (8.2 g, 16%; M.P.: 68° C.) as a pale yellow solid.

Following intermediate was prepared according to the previous procedure:

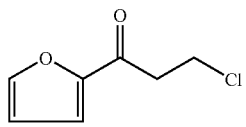

Intermediate 41 The residue (20.0 g) was used for the next step without further purification.

b) Preparation of intermediate 6

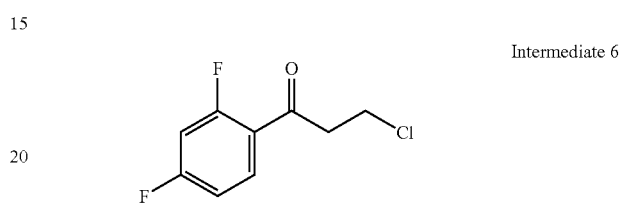

Intermediate 6

Aluminium chloride (0.3 mol) was added carefully to 1,3-difluorobenzene (0.26 mol) and they were heated with vigorously stirring till 50° C. 3-chloropropanoyl chloride (0.26 mol) was added dropwise over a 15 minute period at 40° C. (cooled on ice) and the mixture was stirred at 50° C. The mixture was poured into water (250 ml), ice (250 g) and HCl (25 ml) and it was stirred for 20 minutes. The formed precipitate was filtered off and extracted with CH₂Cl₂ and water. Yield: 40 g of intermediate 6 (75%).

EXAMPLE A5 a) Preparation of intermediate 7

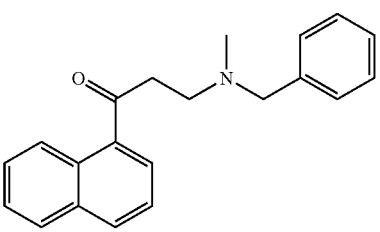

Intermediate 7

A mixture of intermediate 4 (3 g; 0.0137 mol), N-benzylmethyl amine (2 ml; 0.0150 mol) in acetonitrile (100 ml) was stirred at 80° C. for 2 hours. At room temperature water was added. The mixture was extracted with CH₂Cl₂. The organic layer was separated and dried (MgSO₄), filtered, and the solvent was evaporated. The residue (6 g) was purified by column chromatography over silica gel (eluent CH₂Cl₂/MeOH: 97/3; 20-45 μm) to afford an oil. Yield: 4.2 g of intermediate 7.

Following intermediate was prepared according to the previous procedure:

| Intermediate 42 | The residue (22.5 g) was purified by column chromatography over silica gel (eluent: CH₂Cl₂/MeOH: 98/2; 20-45 μm) to afford an oil. Yield: 5.1 g of intermediate 42 (17%). | 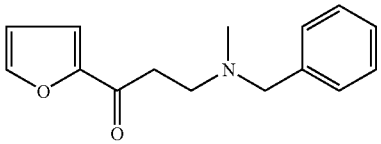<br>Intermediate 42 |
|---|---|---| b) Preparation of intermediate 8

Intermediate 8

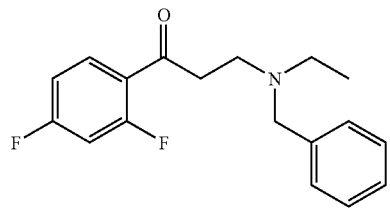

A mixture of intermediate 6 (0.015 mol), N-ethylbenzenemethanamine (0.016 mol) and K₂CO₃ (0.016 mol) in acetonitrile (30 ml) was stirred at 70° C. for 2 hours, poured out into H₂O and extracted with CH₂Cl₂. The organic layer was separated, dried (MgSO₄), filtered, and the solvent was evaporated. Yield: 4 g of intermediate 8 (88%).

EXAMPLE A6 a) Preparation of intermediate 9

Intermediate 9

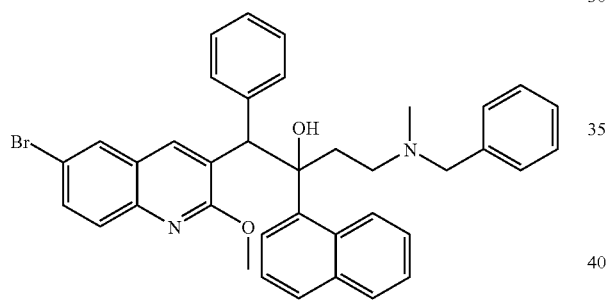

n-Butyl lithium (0.0075 mol) was added at −20° C. to a solution of diisopropylamine (0.0075 mol) in THF (50 ml). The mixture was cooled to −70° C. Intermediate 3 (0.0062 mol) was added. The mixture was stirred at −70° C. for 1 hour and 30 minutes. Intermediate 7 (0.0075 mol) was added. The mixture was stirred for 1 hour and 30 minutes. H₂O was added. The mixture was extracted with CH₂Cl₂. The organic layer was separated, dried (MgSO₄), filtered, and the solvent was evaporated. The residue (3 g) was purified by column chromatography over silica gel (eluent cyclohexane/EtOAc 90/10; 15-40 μm). The pure fractions were collected and the solvent was evaporated. Yield: 1.5 g of a mixture of two diastereoisomers (38%), i.e. intermediate 9.

Following intermediate was prepared according to the previous procedure:

| Intermediate 43 | The residue (7.5 g) was purified by column chromatography over silica gel (eluent: cyclohexane/EtOAc 92/8; 15-40 μm). The pure fractions were collected and the solvent was evaporated. Yield: 3.25 g of intermediate 43 a mixture of two diastereoisomers (55%, mixture of diastereoisomers: 65/35). | 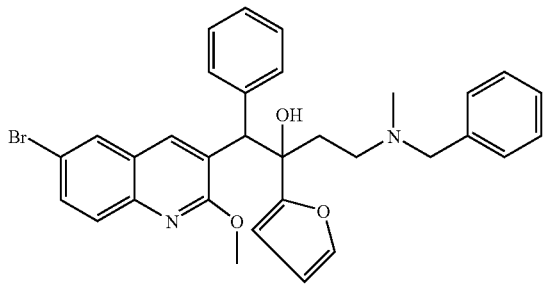<br>Intermediate 43 |
|---|---|---| b) Preparation of intermediate 10

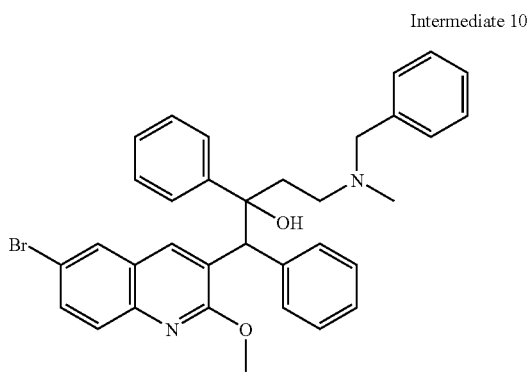

Intermediate 10 n-Butyl lithium (0.0075 mol) was added at −20° C. to a solution of diisopropylamine (0.0075 mol) in THF (50 ml). The mixture was cooled to −70° C. Intermediate 3 (0.0061 mol) was added. The mixture was stirred at −70° C. for 1 hour and 30 minutes. 4-[methyl(phenylmethyl)amino]-1-phenyl-1-butanone (0.0073 mol) was added. The mixture was stirred for 1 hour and 30 minutes. $H_2O$ was added. The mixture was extracted with $CH_2Cl_2$. The organic layer was separated, dried ($MgSO_4$), filtered, and the solvent was evaporated. The residue (4.9 g) was purified by column chromatography over silica gel (eluent: 100% $CH_2Cl_2$; 15-40 μm). The pure fractions were collected and the solvent was evaporated, yielding: 1.43 g of a intermediate 10 (40%, mixture of diastereoisomers: 60/40).

Following intermediates were prepared according to the previous procedure:

| | | |
|---|---|---|
| Intermediate 19 | The residue (6.4 g) was purified by column chromatography over silica gel (eluent: $CH_2Cl_2$/cyclohexane 85/15; 15-40 μm). The pure fractions were collected and the solvent was evaporated, yielding 0.81 g of the intermediate as a mixture of diastereoisomers (44/56) (17%). | 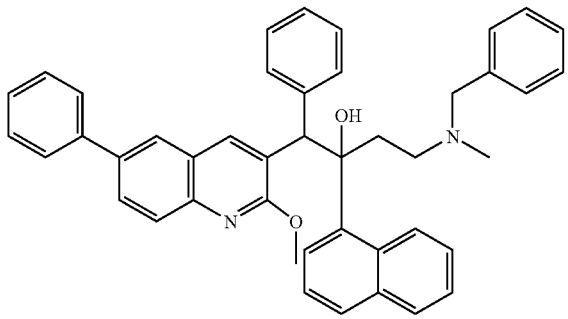<br>Intermediate 19 |
| Intermediate 20 | The residue was purified by column chromatography over silica gel (eluent: cyclohexane/EtOAc 95/5; 15-40 μm). The pure fractions were collected and the solvent was evaporated. Yield: 0.55 g of the intermediate as a mixture of diastereoisomers (12%). | 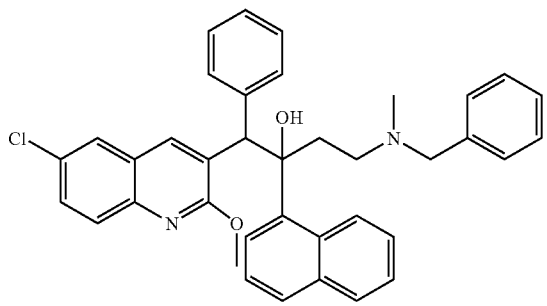<br>Intermediate 20 |
| Intermediate 21 | The residue was purified by column chromatography over silica gel (eluent: cyclohexane/EtOAc 95/5; 15-40 μm). The pure fractions were collected and the solvent was evaporated, to give 0.34 g of the intermediate as a mixture of diastereoisomers (7%). | 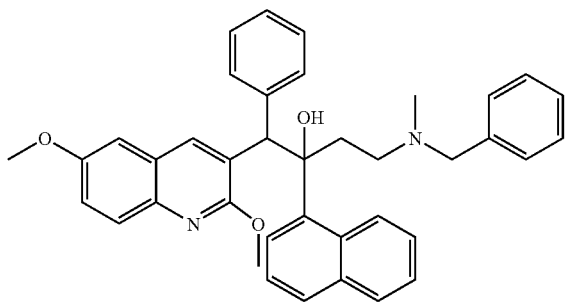<br>Intermediate 21 |

-continued

| | | |
|---|---|---|
| Intermediate 22 | The residue was purified by column chromatography over silica gel (eluent: cyclohexane/EtOAc 95/5; 15-40 μm). The pure fractions were collected and the solvent was evaporated, yielding 0.80 g of the intermediate as a mixture of diastereoisomers (13%). | 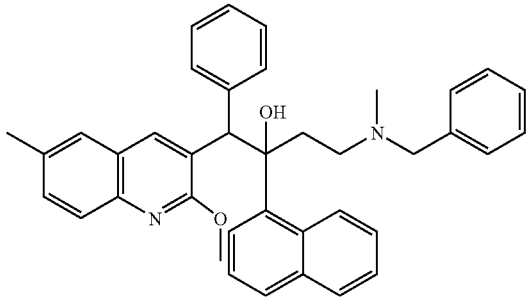<br>Intermediate 22 |
| Intermediate 23 | The residue was purified by column chromatography over silica gel (eluent: cyclohexane/EtOAc 80/20; 15-40 μm).). The pure fractions were collected and the solvent was evaporated. The residue (1.3 g) was purified by column chromatography over silica gel (eluent: acetonitrile/NH₄CO₃ 0.5% 95/5; kromasil). The pure fractions were collected and the solvent was evaporated, affording 0.61 g of the intermediate as a mixture of diastereoisomers (41/59) (18%). | 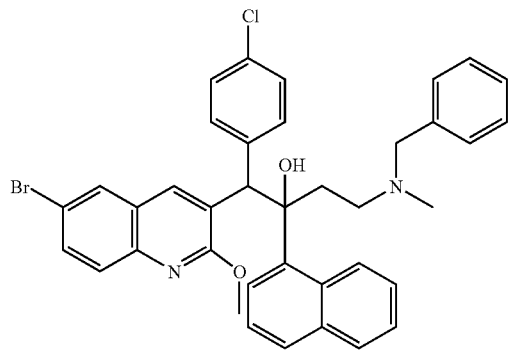<br>Intermediate 23 | c) Preparation of intermediates 11 and 12

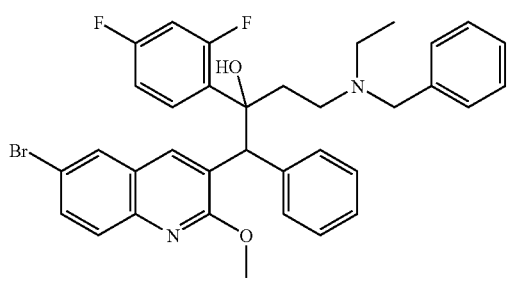

Intermediate 11 (dia A) and
Intermediate 12 (dia B)

n-Butyl lithium (0.0075 mol) was added at −20° C. to a solution of diisopropylamine (0.0075 mol) in THF (50 ml). The mixture was cooled to −70° C. Intermediate 3 (0.00824 mol) was added. The mixture was stirred at −70° C. for 1 hour and 30 minutes. Intermediate 8 (0.0099 mol) was added. The mixture was stirred for 1 hour and 30 minutes. H₂O was added. The mixture was extracted with CH₂Cl₂. The organic layer was separated, dried (MgSO₄), filtered, and the solvent was evaporated. The residue (5.4 g) was purified by column chromatography over silica gel (eluent: CH₂Cl₂/cyclohexane 60/40; 15-40 μm). Two fractions were collected and the solvent was evaporated. Yielding: 0.95 g of intermediate 11 as diastereoisomer A (15%, M.P.: 171° C.) and 0.83 g of intermediate 12 as diastereoisomer B (13%, MH+: 631).

EXAMPLE A7

Preparation of intermediate 17

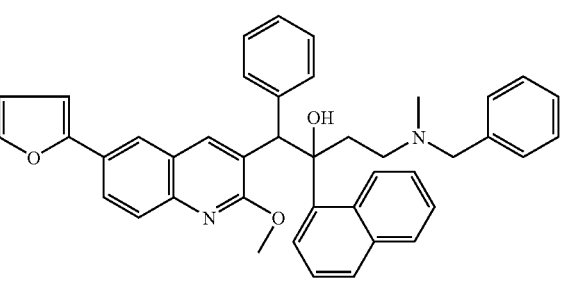

Intermediate 17

Intermediate 9 (1.58 mmol), 2-furanboronic acid (2.69 mmol), Pd(PPh₃)₄ (0.158 mmol), DME (30 ml), MeOH (10 ml) and K₂CO₃ (1.6 ml) were heated under microwaves (300 W, 68° C.) for 10 minutes. The mixture was cooled, poured into water and extracted with EtOAc. The organic layer was separated, dried (MgSO₄), filtered, and the solvent was evaporated. The residue (1.4 g) was purified by column chromatography over silica gel (eluent: cyclohexane/EtOAc 90/10; 15-40 μm). The pure fractions were collected and the solvent was evaporated. Yield. 0.47 g of intermediate 17 as a mixture of diastereoisomers (60/40) (41%).

EXAMPLE A8 a-1) Preparation of intermediates 13 and 14

Intermediate 13

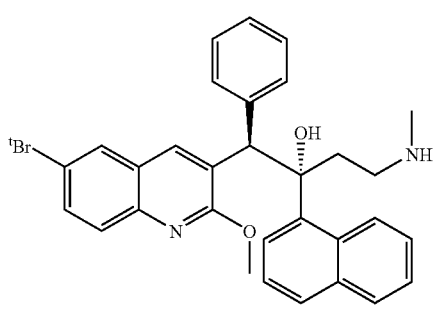

(diastereoisomer A)

Intermediate 14

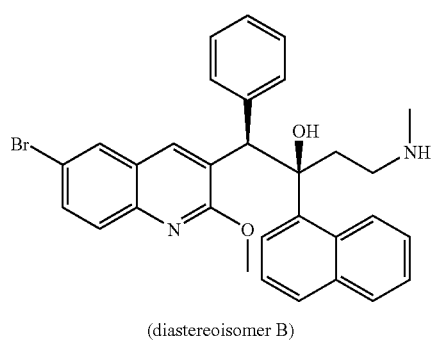

(diastereoisomer B)

1-Chloroethyl chloroformate (15 ml) was added at room temperature to a mixture of intermediate 9 (0.0023 mol) in 1,2-chloroethane (30 ml). The mixture was stirred at 80° C. for 1 hour. The solvent was evaporated. MeOH (15 ml) was added. The mixture was stirred and refluxed for 30 minutes. The solvent was evaporated. The residue (*) (1.49 g) was purified by column chromatography over silica gel (eluent: $CH_2Cl_2$/MeOH/$NH_4OH$ 97/3/0.1; 15-40 µm). Two fractions were collected and the solvent was evaporated. The first residue (0.23 g) was crystallized from DIPE. The precipitate was filtered off and dried, yielding: 0.168 g (13%) of intermediate 13 (diastereoisomer A) (M.P.: 204° C.). The second residue (0.32 g) was crystallized from DIPE. The precipitate was filtered off and dried. Yield: 0.298 g (23%) of intermediate 14 (diastereoisomer B) (M.P.: 225° C.).

Following intermediates were prepared according to the above procedure. The purification of the resulting residue (*) is indicated for each intermediate separately.

| Intermediate 25 and Intermediate 26 | The residue (1,2 g) was purified by column chromatography over silica gel (eluent: $CH_2Cl_2$/MeOH/$NH_4OH$ 95/5/0.1; 15-40 µm). Two fractions were collected and the solvent was evaporated. Yield: 0.047 g of intermediate 25 (diastereoisomer A) (6%, MH+: 491). | 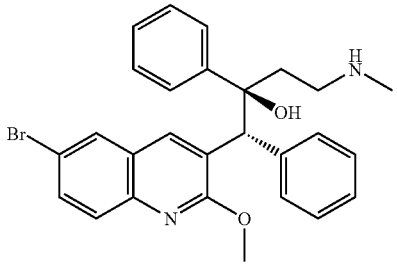 Intermediate 25 (diastereoisomer A) |
|---|---|---|
| | The second residue (0.08 g, 10%) was crystallized from DIPE. The precipitate was filtered off and dried. Yield: 0.031 g of intermediate 26 (diastereoisomer B) (4%, M.P.: 197° C.). | 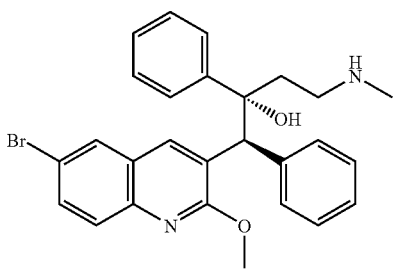 Intermediate 26 (diastereoisomer B) |

-continued

| | | |
|---|---|---|
| Intermediate 27 and Intermediate 28 | The residue (1.0 g) was purified by column chromatography over silica gel (eluent: CH$_2$Cl$_2$/MeOH/NH$_4$OH 96/4/0.1; 15-40 μm). Two fractions were collected and the solvent was evaporated. | 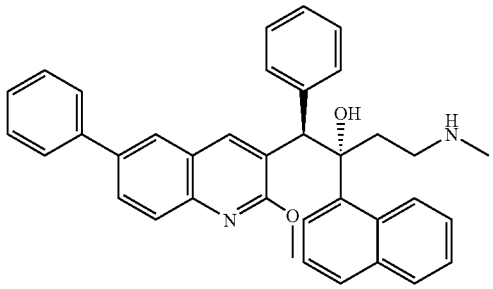<br>Intermediate 27 (diastereoisomer A) |
| | Yield: 0.105 g of intermediate 27 (diastereoisomer A) (15% MH+: 539) and 0.11 g of intermediate 28 (diastereoisomer B) (16%, M.P.: 222° C.). | 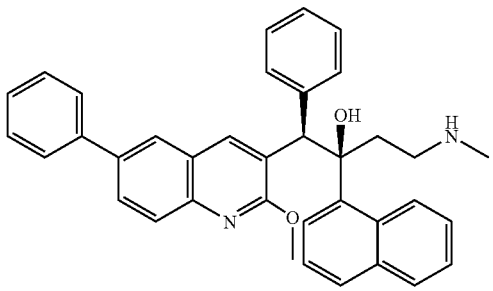<br>Intermediate 28 (diastereoisomer B) |
| Intermediate 29 and Intermediate 30 | The residue (0.5 g) was purified by column chromatography over silica gel (eluent: CH$_2$Cl$_2$/MeOH/NH$_4$OH 97/3/0.1; 10 μm). Two fraction were collected and the solvent was evaporated. | 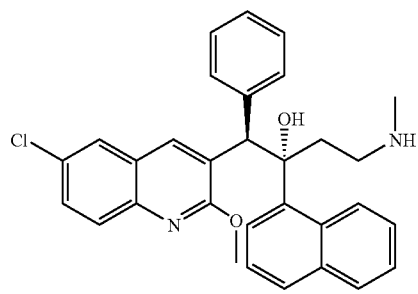<br>Intermediate 29 (diastereoisomer A) |
| | Yield: 0.11 g of intermediate 29 (diastereoisomer A) (24%, MH+: 497) and 0.10 g of intermediate 30 (diastereoisomer B) (22%, MH+: 497). | 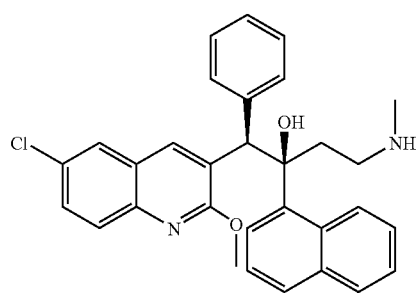<br>Intermediate 30 (diastereoisomer B) |
| Intermediate 31 and Intermediate 32 | The residue (0.32 g) was purified by column chromatography over silica gel (eluent: CH$_2$Cl$_2$/MeOH/NH$_4$OH 97/3/0.1; 10 μm). Two fractions were collected and the solvent was evaporated. | 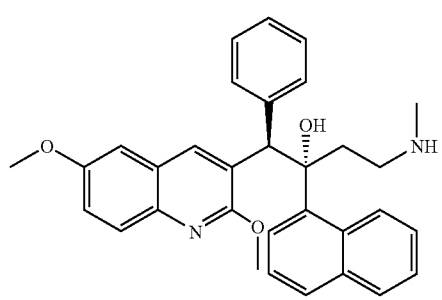<br>Intermediate 31 (diastereoisomer A) |

-continued

Yield: 0.10 g of
intermediate 31 (diastereoisomer A)
(35%, MH+: 493) and 0.04 g of
intermediate 32 (diastereoisomer B)
(14%, MH+: 493).

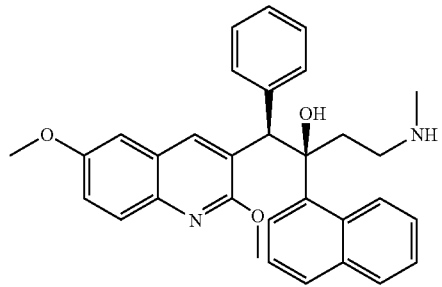

Intermediate 32 (diastereoisomer B)

| Intermediate 33 and Intermediate 34 | The residue (0.9 g) was purified by column chromatography over silica gel (eluent: CH₂Cl₂/MeOH/NH₄OH 98/2/0.1; 10 µm). Two fractions were collected and the solvent was evaporated. |

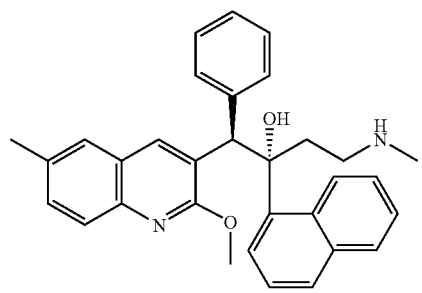

Intermediate 33 (diastereoisomer A)

Yield: 0.09 g of
intermediate 33 (diastereoisomer A)
(15%, MH+: 477) and 0.08 g of
intermediate 34 (diastereoisomer B)
(13%, MH+: 477).

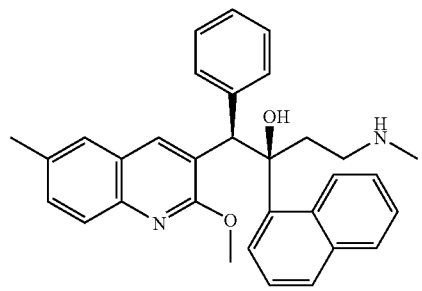

Intermediate 34 (diastereoisomer B)

| Intermediate 35 and Intermediate 36 | The residue (0.45 g) was purified by column chromatography over silica gel (eluent: CH₂Cl₂/MeOH/NH₄OH 96/4/0.1; 10 µm). Two fractions were collected and the solvent was evaporated. |

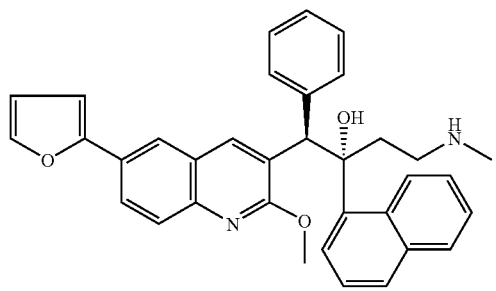

Intermediate 35 (diastereoisomer A)

| | | |
|---|---|---|
| | Yield: 0.09 g of intermediate 35 (diastereoisomer A) (22%, MH+: 529) and 0.12 g of intermediate 36 (diastereoisomer B) (30%, MH+: 529). | 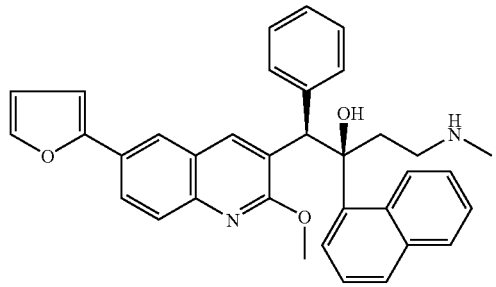<br>Intermediate 36 (diastereoisomer B) |
| Intermediate 37 and Intermediate 38 | The residue (0.63 g) was purified by column chromatography over silica gel (eluent: CH$_2$Cl$_2$/MeOH/NH$_4$OH 98/2/0.1; 15-40 μm). Two fractions were collected and the solvent was evaporated. | 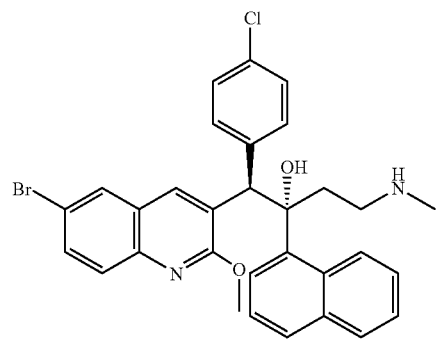<br>Intermediate 37 (diastereoisomer A) |
| | Yield: 0.08 g of intermediate 37 (diastereomer A) (15%, MH+: 575) and 0.06 g of intermediate 38 (diastereoisomer B) (12%, MH+: 575). | 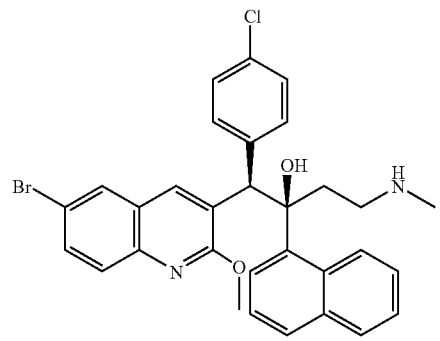<br>Intermediate 38 (diastereoisomer B) |
| Intermediate 39 | The residue (0.92 g) was purified by column chromatography over silica gel (eluent: CH$_2$Cl$_2$/MeOH 95/5; 15-40 μm). The pure fractions were collected and the solvent was evaporated. Yielding: 0.4 g of intermediate 39 (diastereoisomer A) (56%, MH+: 541). | 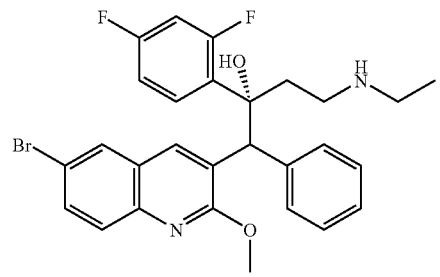<br>Intermediate 39 (diastereoisomer A) |

| | |
|---|---|
| Intermediate 40 | The residue (0.49 g) was purified by column chromatography over silica gel (eluent: CH$_2$Cl$_2$/MeOH/NH$_4$OH 96/4/0.1; 15-40 μm). The pure fractions were collected and the solvent was evaporated. Yielding: 0.265 g of intermediate 40 (diastereoisomer B) (66%, MH+: 541). |

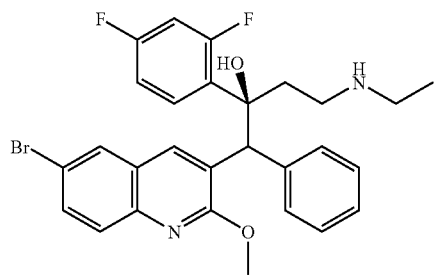

Intermediate 40 (diastereoisomer B)

a-2) Preparation of intermediates 15 and 16

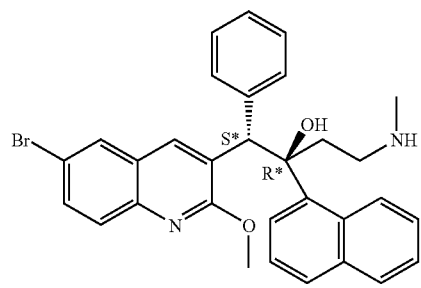

Intermediate 15

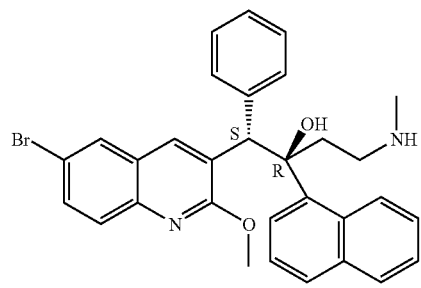

Intermediate 16

Intermediate 13 (diastereoisomer A) (0.9 g) was purified by chiral chromatography over silica gel (eluent: 100% ethanol). Two fractions were collected and the solvent was evaporated. Yield: 0.420 g of intermediate 15 (enantiomer A1) (M.P.: 161° C., MH+: 541) and 0.397 g of intermediate 16 (enantiomer A2) (M.P.: 158° C., MH+: 541).

a-3) Preparation of intermediates 44 and 45

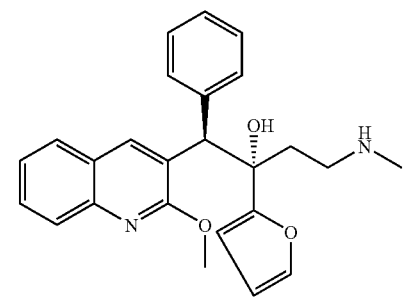

Intermediate 44

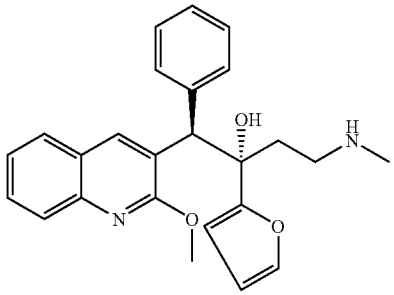

Intermediate 45

A mixture of intermediate 43 (prepared according to A6.a) (1.5 g, 2.62 mol), ammonium formate (0.83 g, 0.013 mol) and palladium on charcoal (10%, 1.5 g) in methanol (30 ml) was heated under reflux for 1 hour. The mixture was cooled and filtered on a short pad of celite. Water was added. The organic layer was extracted with ethyl acetate, separated, dried (MgSO$_4$), filtered, and the solvent was evaporated. The residue (1.3 g) was purified by column chromatography over silica gel (eluent: MeOH/AcNH$_4$: 60/40, kromasil C$_{18}$, 5 μm) The pure fractions were collected and the solvent was evaporated yielding two fractions. Yield: 0.14 g of intermediate 44 as diastereoisomer A (12%) and 0.26 g of intermediate 45 as diastereoisomer B (22%).

EXAMPLE A9

Preparation of intermediate 18

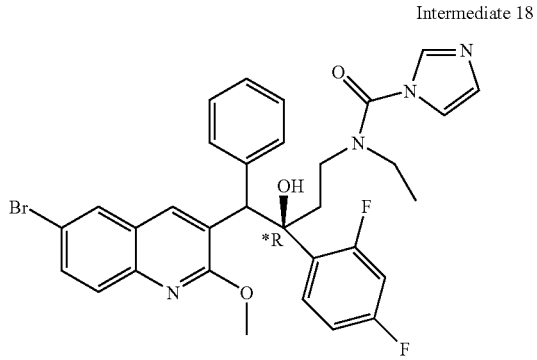

Intermediate 18

A mixture of the intermediate 39 prepared according to example A8.a-1) (0.0002 mol) and CDI (0.0003 mol) in THF (7 ml) was stirred and refluxed for 2 hours, poured out into H$_2$O and extracted with CH$_2$Cl$_2$. The organic layer was separated, dried (MgSO$_4$), filtered, and the solvent was evaporated. Yield: 0.15 g of intermediate 18 (diastereoisomer A) (84%).

B. Preparation of the Compounds

EXAMPLE B1

Preparation of compound 1

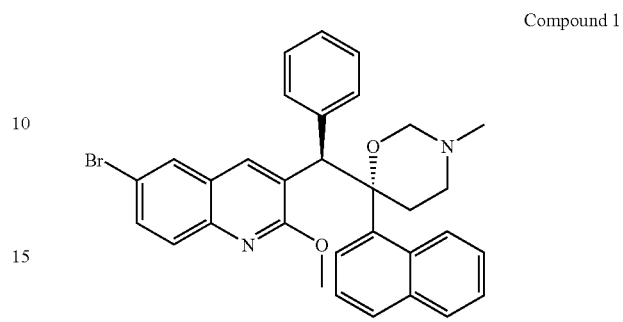

Compound 1

A mixture of intermediate 13 (prepared according to example A8. a-1) (0.00009 mol) and paraformaldehyde (0.0001 mol) in toluene (5 ml) was stirred at 80° C. The mixture was evaporated. The residue (*) was purified by column chromatography over silica gel (eluent: CH$_2$Cl$_2$/MeOH 99/1; 15-40 μm). The pure fractions were collected and the solvent was evaporated. Yield: 0.025 g of compound 1 (diastereoisomer A) (49%, M.P.: 112° C.).

Following compounds were prepared according to the above procedure. The purification of the residue (*) is indicated if different from the above-described purification.

| | |
|---|---|
| Compound 6 | 0.068 g of diastereoisomer A (69%, MH+: 551) |

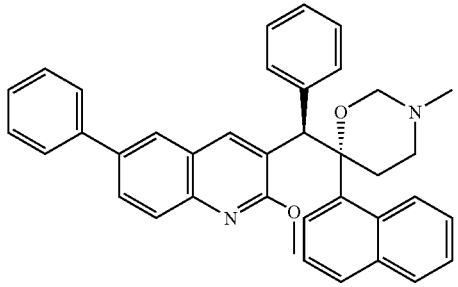

Compound 6 (diastereoisomer A)

| | |
|---|---|
| Compound 7 | 0.11 g of diastereoisomer A (98%, MH+: 509) |

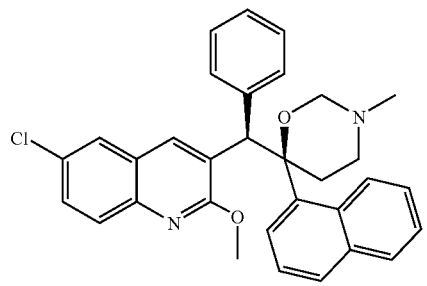

Compound 7 (diastereoisomer A)

-continued

| | | |
|---|---|---|
| Compound 8 | 0.08 g of diastereoisomer A (80%, MH+: 505) | 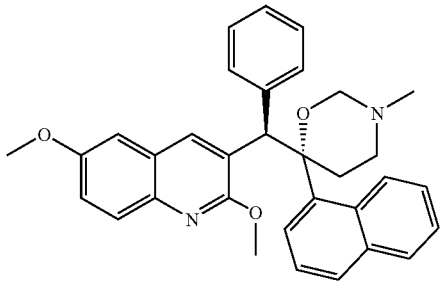<br>Compound 8 (diastereoisomer A) |
| Compound 9 | 0.082 g of diastereoisomer A (100%, MH+: 489) | 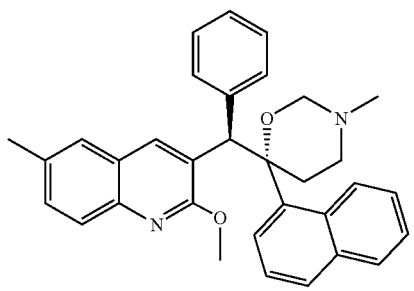<br>Compound 9 (diastereoisomer A) |
| Compound 10 | 0.082 g of diastereoisomer A (89%, MH+: 541) | 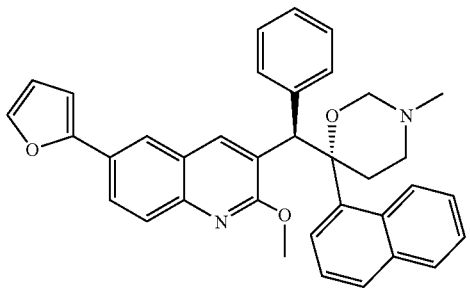<br>Compound 10 (diastereoisomer A) |
| Compound 11 | The residue was purified by column chromatography over silica gel (eluent: CH$_2$Cl$_2$/MeOH 99/1; 15-40 µm). The pure fractions were collected and the solvent was evaporated. Yield: 0.036 g of diastereoisomer B (71%, M.P.: 108° C.). | 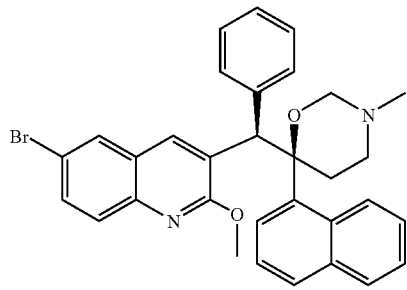<br>Compound 11 (diastereoisomer B) |

-continued
| Compound 12 | 0.045 g of diastereoisomer B (88%, M.P.: 168° C.) | 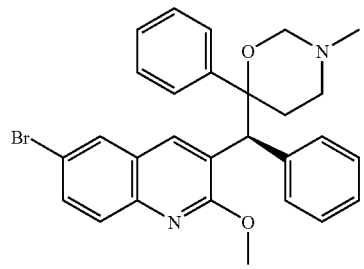
Compound 12 (diastereoisomer B) |
| Compound 13 | 0.077 g diastereoisomer B (61%, MH+: 551). | 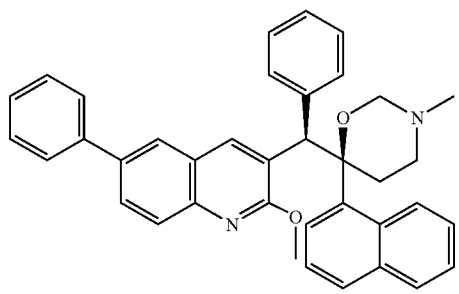
Compound 13 (diastereoisomer B) |
| Compound 14 | 0.040 g of diastereoisomer B (100%, MH+: 505). | 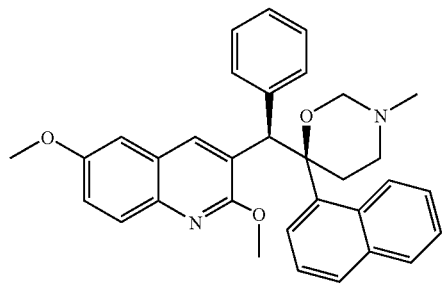
Compound 14 (diastereoisomer B) |
| Compound 15 | 0.044 g of diastereoisomer B (72%, MH+: 489). | 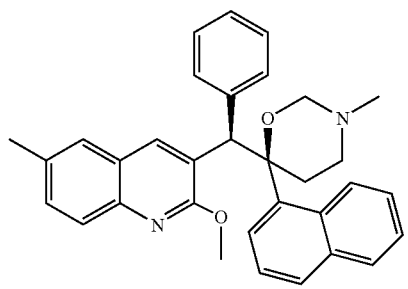
Compound 15 (diastereoisomer B) |

| | |
|---|---|
| Compound 16 | 012 g of diastereoisomer B (98%, MH+: 541). |

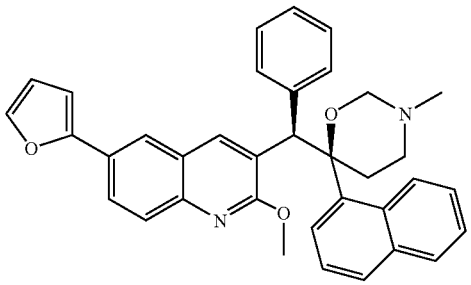

Compound 16 (diastereoisomer B)

| | |
|---|---|
| Compound 17 | 0.034 g of diastereoisomer B (90%, MH+: 587). |

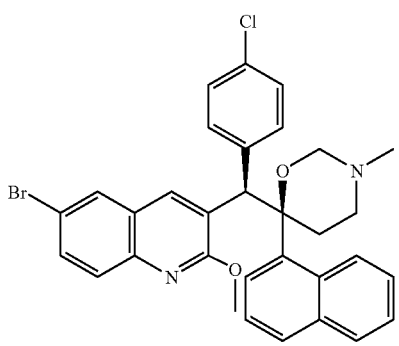

Compound 17 (diastereoisomer B)

EXAMPLE B2

Preparation of compound 2

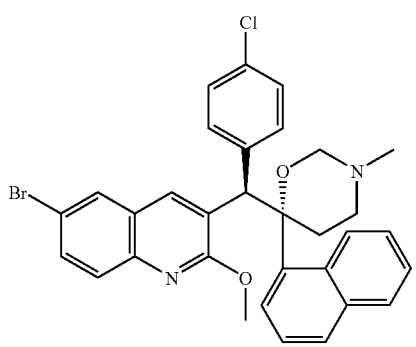

Compound 2

A mixture of intermediate 37 (diastereoisomer A prepared according to example A8.a-1) (0.00009 mol) and paraformaldehyde (0.0001 mol) in toluene (5 ml) was stirred at 80° C. The mixture was evaporated. The residue was purified by column chromatography over silica gel (eluent: CH$_2$Cl$_2$/MeOH 99/1; 15-40 μm). The pure fractions were collected and the solvent was evaporated. The residue (0.06 g, 92%) was crystallized from DIPE. The precipitate was filtered off and dried. Yield: 0.026 g of compound 2 (diastereoisomer A) (40%, M.P.: 201° C.).

EXAMPLE B3

Preparation of compound 3

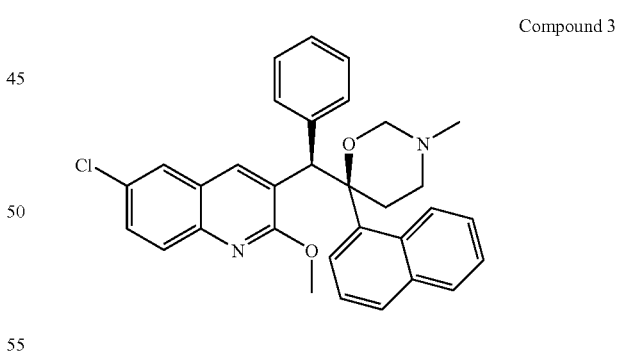

Compound 3

A mixture of intermediate 30 (diastereoisomer B prepared according to example A8.a-1) (0.00009 mol) and paraformaldehyde (0.0001 mol) in toluene (5 ml) was stirred at 80° C. The mixture was evaporated. The residue was purified by column chromatography over silica gel (eluent: CH$_2$Cl$_2$MeOH 99/1; 15-40 μm). The pure fractions were collected and the solvent was evaporated. The residue (0.11 g, 100%) was crystallized from diethyl ether. The precipitate was filtered off and dried. Yielding: 0.033 g of compound 3 (diastereoisomer B) (33%, M.P.: 189° C.).

EXAMPLE B4

Preparation of compound 4

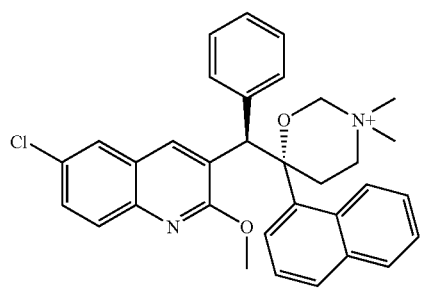

Compound 4

A mixture of compound 7 (diastereoisomer A prepared according to example B1) (0.1 mmol) and iodomethane (0.1 mmol) in acetone (2 ml) was stirred at room temperature for 2.5 hours. The precipitate was filtered, washed with acetone and dried. Yield: 0.031 g compound 4 as a hydroiodide (diastereoisomer A) (48%, M.P.: 211° C.)

Following compound was prepared according to the previous procedure:

EXAMPLE B5

Preparation of compound 5

Compound 5

Sodium hydride (0.011 g) was added at 0° C. to a mixture of intermediate 18 (prepared according to example A9) (0.0001 mol) in THF (10 ml) under $N_2$ flow. The mixture was stirred at 0° C. for 30 minutes, poured out into $H_2O$ and extracted with EtOAc. The organic layer was separated, dried ($MgSO_4$), filtered, and the solvent was evaporated. The residue was purified by column chromatography over silica gel (eluent: cyclohexane/EtOAc 80/20; 15-40 µm). The pure fractions were collected and the solvent was evaporated. The residue (0.09 g, 67%) was crystallized from DIPE. The precipitate was filtered off and dried. Yield: 0.034 g of compound 5 (diastereoisomer A) (M.P.: 192° C.).

Following compound was prepared according to the previous procedure:

| | |
|---|---|
| Compound 18 | 0.046 g of diastereoisomer B as a hydroiodide (71%, M.P.: 195° C.). |

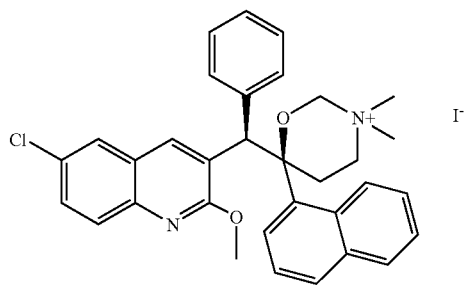

Compound 18 (diastereoisomer B)

| Compound 19 | 0.047 g of diastereoisomer B (M.P.: 216° C.). |

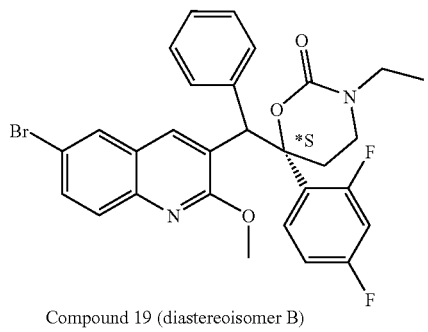

Compound 19 (diastereoisomer B)

EXAMPLE B6

Preparation of compound 20

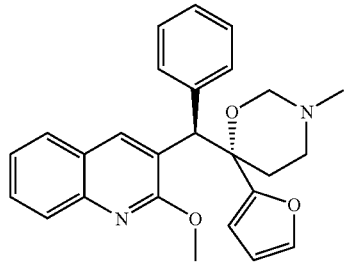

Compound 20

A mixture of intermediate 44 (diastereoisomer A prepared according to example A8a-3) (0.12 g, 0.298 mmol) and paraformaldehyde (0.358 mmol) in toluene (5 ml) was stirred at 80° C. for 2 hours. Water was added at room temperature and the organic layer was extracted with ethyl acetate, separated, dried (MgSO$_4$), filtered, and the solvent was evaporated. The residue (0.13 g) was purified by column chromatography over silica gel (eluent: CH$_2$Cl$_2$/CH$_3$OH/NH$_4$OH: 99/1/0.1, 10 μm). The pure fractions were collected and the solvent was evaporated. Yield: 0.075 g of compound 20 (diastereoisomer A) (61%, MH+: 415).

Following compound was prepared according to the previous procedure but without the column chromatography:

| Compound 21 | 0.095 g of diastereoisomer B (93%, MH+: 415). |

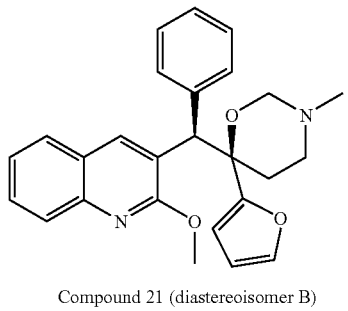

Compound 21 (diastereoisomer B)

C. Analytical Methods

The mass of the compounds was recorded with LCMS (liquid chromatography mass spectrometry). Three methods were used which are described below. The data are gathered in Table 1 below.

LCMS-method 1

LCMS analysis was carried out (electrospray ionization in positive mode, scanning mode from 100 to 900 amu) on a Kromasil C18 column (Interchim, Montlucon, FR; 5 μm, 4.6×150 mm) with a flow rate of 1 ml/minute. Two mobile phases (mobile phase A: 30% 6.5 mM ammonium acetate+40% acetonitrile+30% formic acid (2 ml/l); mobile phase B: 100% acetonitrile) were employed to run a gradient condition from 100% A for 1 minute to 100% B in 4 minutes, 100% B for 5 minutes to 100% A in 3 minutes, and reequilibrate with 100% A for 2 minutes.

LCMS-method 2

LCMS analysis was carried out (electrospray ionization in both positive and negative (pulsed) mode scanning from 100 to 1000 amu) on a Kromasil C18 column (Interchim, Montlucon, FR; 3.5 μm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

LCMS-method 3

LCMS analysis was carried out (electrospray ionization in both positive and negative (pulsed) mode scanning from 100 to 1000 amu) on a Sunfire C18 column (Waters, Millford USA; 3.5 μm, 4.6×100 mm) with a flow rate of 0.8 ml/minute. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

LCMS-method 4

LCMS analysis was carried out (electrospray ionization in both positive and negative (pulsed) mode scanning from 100 to 1000 amu) on a Sunfire C18 column (Waters, Millford USA; 3.5 μm, 4.6×100 mm) with a flow rate of 0.8 ml/minute. Two mobile phases (mobile phase A: 25% 6.5 mM ammonium acetate+50% acetonitrile+25% formic acid (2 ml/l); mobile phase B: 100% acetonitrile) were employed to run a gradient condition from 100% A for 1 minute to 100% B in 4 minutes, 100% B at a flow rate of 1.2 ml/minute for 4 minutes to 100% A at 0.8 ml/minute in 3 minutes, and reequilibrate with 100% A for 1.5 minute.

TABLE 1

LCMS parent peak

| No. | LCMS-method |
|---|---|
| Intermediate 11 | 1 |
| Intermediate 12 | 1 |
| Intermediate 26 | 1 |
| Intermediate 27 | 3 |
| Intermediate 28 | 3 |
| Intermediate 33 | 1 |
| Intermediate 34 | 1 |
| Intermediate 37 | 3 |
| Intermediate 39 | 1 |
| Intermediate 44 | 2 |
| Intermediate 45 | 2 |
| Compound 1 | 1 |
| Compound 2 | 3 |
| Compound 3 | 2 |
| Compound 4 | 1 |
| Compound 5 | 1 |
| Compound 6 | 3 |
| Compound 7 | 2 |
| Compound 8 | 2 |
| Compound 9 | 3 |
| Compound 10 | 3 |
| Compound 12 | 1 |
| Compound 13 | 3 |
| Compound 14 | 2 |
| Compound 15 | 3 |
| Compound 16 | 3 |
| Compound 17 | 3 |
| Compound 18 | 1 |
| Compound 19 | 1 |
| Compound 20 | 4 |
| Compound 21 | 4 |

D. Pharmacological Examples

D.1. In-vitro method for testing compounds against *M. tuberculosis*.

Flat-bottom, sterile 96-well plastic microtiter plates were filled with 100 µl of Middlebrook (1×) broth medium. Subsequently, stock solutions (10× final test concentration) of compounds were added in 25 µl volumes to a series of duplicate wells in column 2 so as to allow evaluation of their effects on bacterial growth. Serial five-fold dilutions were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 5000 CFU per well of *Mycobacterium tuberculosis* (strain H37RV), in a volume of 100 µl in Middlebrook (1×) broth medium was added to the rows A to H, except column 12. The same volume of broth medium without inoculum was added to column 12 in row A to H. The cultures were incubated at 37° C. for 7 days in a humidified atmosphere (incubator with open air valve and continuous ventilation). One day before the end of incubation, 6 days after inoculation, Resazurin (1:5) was added to all wells in a volume of 20 µl and plates were incubated for another 24 hours at 37° C. On day 7 the bacterial growth was quantitated fluorometrically.

The fluorescence was read in a computer-controlled fluorometer (Spectramax Gemini EM, Molecular Devices) at an excitation wavelength of 530 nm and an emission wavelength of 590 nm. The percentage growth inhibition achieved by the compounds was calculated according to standard methods, and MIC data (representing IC90's expressed in microgram/ml) were calculated.

D.2. In-vitro method for testing compounds for antibacterial activity against strain *M. Smegmatis* ATCC607.

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 µl in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 µl and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The % growth inhibition achieved by the compounds was calculated according to standard methods. The $pIC_{50}$ was defined as the 50% inhibitory concentration for bacterial growth. The results are shown in Table 2.

TABLE 2

Results of in vitro-screening of the compounds according to the invention for *M. smegmatis* ($pIC_{50}$).

| Compound No. | $pIC_{50}$ |
|---|---|
| 1 | 8.5 |
| 2 | 7.2 |
| 3 | 5.1 |
| 5 | 4.7 |
| 6 | 7.6 |
| 7 | 7.9 |
| 8 | 7.2 |
| 11 | 6.5 |
| 12 | 6.8 |
| 13 | 6.5 |
| 14 | 6.5 |
| 16 | 6.5 |
| 17 | 6.5 |

The invention claimed is:
1. A compound of formula

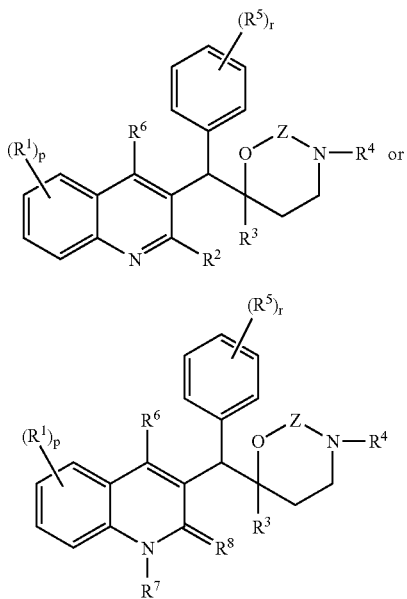

the pharmaceutically acceptable acid or base addition salts thereof, the quaternary amines thereof, the stereochemically isomeric forms thereof, the tautomeric forms thereof and the N-oxide forms thereof, wherein:

$R^1$ is hydrogen, halo, haloalkyl, cyano, hydroxy, Ar, Het, alkyl, alkyloxy, alkylthio, alkyloxyalkyl, alkylthioalkyl, Ar-alkyl or di(Ar)alkyl;

p is an integer equal to 1,2, 3 or 4;

$R^2$ is hydrogen, hydroxy, alkyloxy, alkyloxyalkyloxy, alkylthio, mono or di(alkyl)amino or a radical of formula

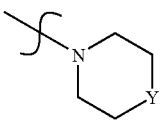

wherein Y is $CH_2$, O, S, NH or N-alkyl;

$R^3$ is alkyl, Ar, Ar-alkyl, Het or Het-alkyl;

$R^4$ is hydrogen, alkyl or benzyl;

$R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl ; or two vicinal $R^5$ radicals may be taken together to form together with the phenyl ring to which they are attached a naphthyl;

r is an integer equal to 1,2,3,4 or 5; and $R^6$ is hydrogen, alkyl, Ar or Het;

$R^7$ is hydrogen or alkyl;

$R^8$ is oxo; or $R^7$ and $R^8$ together form the radical —CH=CH—N=;

Z is $CH_2$ or C(=O);

Ar is a homocycle selected from the group of phenyl, naphthyl, acenaphthyl, tetrahydronaphthyl, each optionally substituted with 1, 2 or 3 substituents, each substituent independently selected from the group of hydroxy, halo, cyano, nitro, amino, mono- or dialkylamino, alkyl, haloalkyl, alkyloxy, haloalkyloxy, carboxyl, alkyloxycarbonyl, aminocarbonyl, morpholinyl and mono- or dialkylaminocarbonyl;

Het is a monocyclic heterocycle selected from the group of N-phenoxypiperidinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl or a bicyclic heterocycle selected from the group of quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4.]dioxinyl or benzo[1,3]dioxolyl; each monocyclic and bicyclic heterocycle may optionally be substituted on a carbon atom with 1, 2 or 3 substituents selected from the group of halo, hydroxy, alkyl or alkyloxy.

2. A compound according to claim 1 wherein Z is $CH_2$.

3. A compound according to claim 1 or 2 wherein $R^5$ is hydrogen, halo, haloalkyl, hydroxy, Ar, alkyl, alkyloxy, alkylthio, alkyloxyalkyl, alkylthioalkyl, Ar-alkyl or di(Ar)alkyl.

4. A compound according to claim 1 or 2 wherein $R^1$ is hydrogen, halo, cyano, Ar, Het, alkyl, and alkyloxy;

p is an integer equal to 1, 2, 3 or 4;

$R^2$ is hydrogen, hydroxy, alkyloxy, alkyloxyalkyloxy, alkylthio or a radical of formula

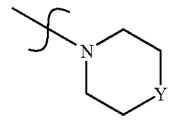

wherein Y is O;

$R^3$ is alkyl, Ar, Ar-alkyl or Het;

$R^4$ is hydrogen, alkyl or benzyl;

$R^5$ is hydrogen, halo or alkyl; or two vicinal $R_5$ radicals may be taken together to form together with the phenyl ring to which they are attached a naphthyl;

r is an integer equal to 1; and $R^6$ is hydrogen;

$R^7$ is hydrogen or alkyl;

$R^8$ is oxo; or $R^7$ and $R^8$ together form the radical —CH=CH—N=;

Ar is a homocycle selected from the group of phenyl, naphthyl, acenaphthyl, tetrahydronaphthyl, each optionally substituted with 1, 2 or 3 substituents, each substituent independently selected from the group of halo, haloalkyl, cyano, alkyloxy and morpholinyl Het is a monocyclic heterocycle selected from the group of N-phenoxypiperidinyl, furanyl, thienyl, pyridinyl, pyrimidiny; or a bicyclic heterocycle selected from the group of benzothienyl, 2,3-dihydrobenzo[1,4]dioxinyl or benzo[1,3]dioxolyl; each monocyclic and bicyclic heterocycle may optionally be substituted on a carbon atom with 1, 2 or 3 alkyl substituents.

5. A compound according to claim 4 wherein the compound is a compound of formula (Ia) and wherein $R^1$ is hydrogen, halo, Ar, Het, alkyl or alkyloxy; p=1; $R^2$ is hydrogen, alkyloxy or alkylthio; $R^3$ is naphthyl, phenyl or Het, each optionally substituted with 1 or 2 substituents selected from the group of halo and haloalkyl; $R^4$ is hydrogen or alkyl; $R^5$ is hydrogen, alkyl or halo; r is equal to 1 and $R^6$ is hydrogen.

6. A compound according to claim 5, wherein the compound is a compound according to formula (Ia) wherein $R^1$ is hydrogen, halo, alkyl, or Het; $R^2$ is alkyloxy; $R^3$ is naphthyl, phenyl or Het, each optionally substituted with halo; $R^4$ is alkyl; $R^5$ is hydrogen or halo; $R^6$ is hydrogen; Z is $CH_2$ or C(=O).

7. A pharmaceutical composition comprising a pharmaceutically acceptable carrier and, as active ingredient, a therapeutically effective amount of a compound as defined in claim 1.

8. A process for preparing a compound according to claim 1, characterized by a) reacting an intermediate of formula (II-a) and (II-b) with paraformaldehyde in a suitable solvent

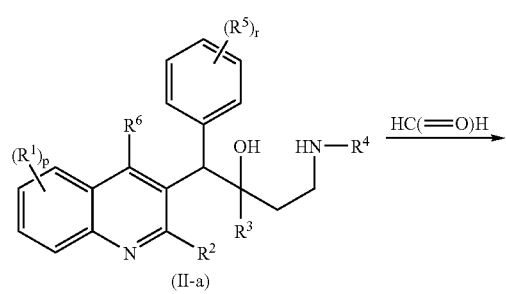
(II-a)

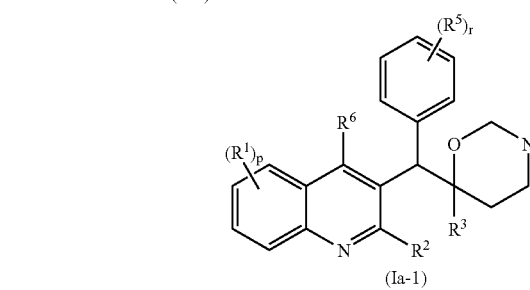
(Ia-1)

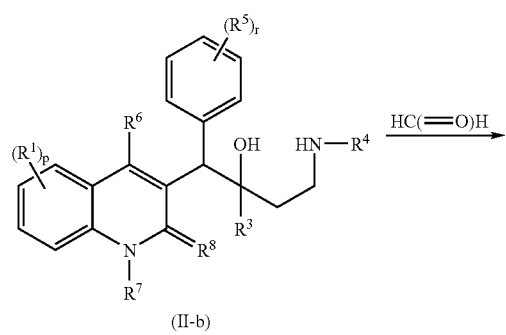
(II-b)

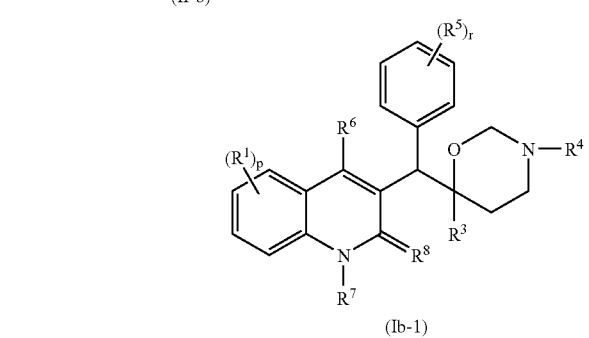
(Ib-1)

with $R^1$ to $R^8$, p and r as defined in claim 1;

b) reacting an intermediate of formula (III-a) and (III-b) with a suitable base in a suitable solvent,

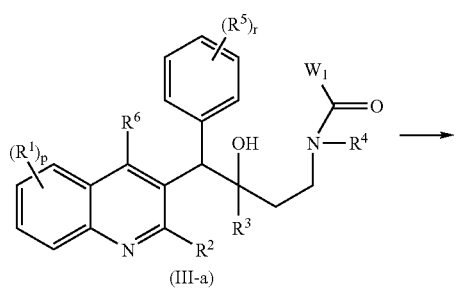
(III-a)

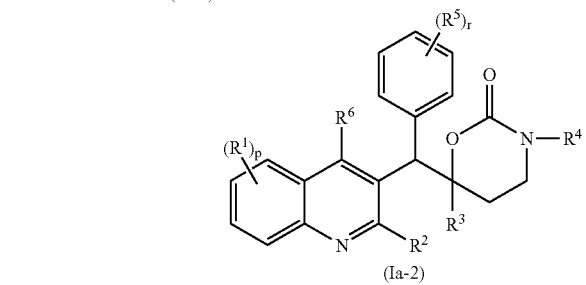
(Ia-2)

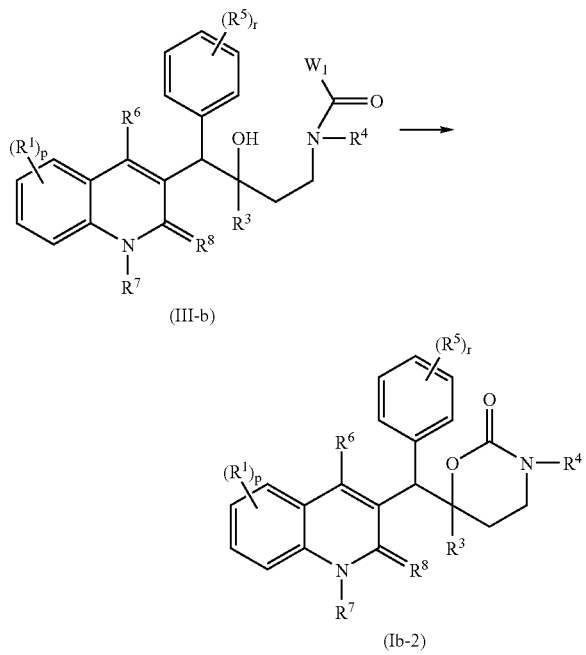
(III-b)

(Ib-2)

with $R^1$ to $R^8$, p and r as defined in claim 1 and $W_1$ representing a suitable leaving group; or, if desired, converting compounds of formula (Ia) or (Ib) into each other following art-known transformations, and further, if desired, converting the compounds of formula (Ia) or (Ib), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms, quaternary amines, tautomeric forms or N-oxide forms thereof.

9. A method of treating a patient having a mycobacterial infection comprising administering a therapeutic amount of a Compound of claim 1 to said patient.

* * * * *